United States Patent
Li et al.

(10) Patent No.: US 9,297,008 B2
(45) Date of Patent: Mar. 29, 2016

(54) SMALL ACTIVATING RNA MOLECULES AND METHODS OF USE

(71) Applicant: The Regents of the University of California, Oakland, CA (US)

(72) Inventors: Longcheng Li, San Francisco, CA (US); Rajvir Dahiya, Pacifica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/504,303

(22) Filed: Oct. 1, 2014

(65) Prior Publication Data

US 2015/0104869 A1 Apr. 16, 2015

Related U.S. Application Data

(63) Continuation of application No. 11/910,722, filed as application No. PCT/US2006/013559 on Apr. 11, 2006, now Pat. No. 8,877,721.

(60) Provisional application No. 60/715,759, filed on Sep. 9, 2005, provisional application No. 60/671,666, filed on Apr. 15, 2005.

(51) Int. Cl.
*A61K 48/00* (2006.01)
*C12N 15/11* (2006.01)
*C07H 21/04* (2006.01)
*C12Q 1/68* (2006.01)
*C12N 15/113* (2010.01)

(52) U.S. Cl.
CPC .......... *C12N 15/113* (2013.01); *C12N 15/1135* (2013.01); *C12N 15/1136* (2013.01); *C12N 15/1138* (2013.01); *C12N 2310/113* (2013.01); *C12N 2310/13* (2013.01); *C12N 2310/53* (2013.01)

(58) Field of Classification Search
None
See application file for complete search history.

(56) References Cited

U.S. PATENT DOCUMENTS

| | | | |
|---|---|---|---|
| 5,614,396 | A | 3/1997 | Bradley et al. |
| 5,624,803 | A | 4/1997 | Noonberg et al. |
| 5,889,136 | A | 3/1999 | Scaringe et al. |
| 6,008,400 | A | 12/1999 | Scaringe et al. |
| 2003/0176384 | A1 | 9/2003 | Uhlmann et al. |
| 2004/0005593 | A1 | 1/2004 | Lorens |
| 2004/0171118 | A1 | 9/2004 | Rossi et al. |
| 2004/0224405 | A1 | 11/2004 | Leake |
| 2005/0048647 | A1 | 3/2005 | Taira et al. |
| 2005/0060771 | A1 | 3/2005 | Farmer |
| 2007/0111963 | A1 | 5/2007 | Corey et al. |

OTHER PUBLICATIONS

Turunen et al., Efficient regulation of VEGF expression by promoter-targeted lentiviral shRNAs based on epigenetic mechanism a novel example of epigenetherapy, 2009, Circulation Research, vol. 105, pp. 604-609.*
Wang et al., Identification of small activating RNAs that enhance endogenous OCT4 expression in human mesenchymal stem cells, 2015, Stem Cells and Development, vol. 24, pp. 345-353.*
Long-Cheng Li, The multifaceted small RNAs, 2008, RNA Biology, vol. 5, pp. 61-64.*
Bannister et al. (2002) "Histone Methylation: Dynamic or Static?" *Cell* 109:801-806.
Britten et al. (1969) "Gene Regulation for Higher Cells: A Theory" *Science* 165(891):349-357.
Brummelkamp et al. (2002) "A System for Stable Expression of Short Interfering RNAs in Mammalian Cells" *Science* 296:497-500.
Buskirk et al. (2003) "In vivo evolution of an RNA-based transcriptional activator" *Chemistry and Biology* 10:533-540.
Dykxhoorn et al. (2003) "Killing the messenger: short RNAs that silence gene expression" *Nature Reviews Molecular Cell Biology* 4:457-467.
Elbashire et al. (2002) "Analysis of gene function in somatic mammalian cells using small interfering RNAs" *Methods* 26:199-213.
Faria et al. (2001) "Phosphoramidate oligonucleotides aspotent antisense molecules in cells and in vivo" *Nature Biotechnology* 19:40-44.
GenBank Accession No. AF095785 (2002).
GenBank Accession No. L34545 (1994).
GenBank Accession No. U24170 (1995).
Huang et al. (2010) "RNAa is conserved in mammalian cells" *PLoS ONE* 5(e8848):1-8.
Hsu et al. (2000) "E-Cadherin Expression in Melanoma Cells Restores Keratinocyte-Mediated Growth Control and DownRegulates Expression of Invasion-Related Adhesion Receptors" *American Journal of Pathology* (156)5:1515-1525.
Jaenisch et al. (2003) "Epigenetic regulation of gene expression: how the genome integrates intrinsic and environmental signals" *Nat Genet* 33 Suppl:245-254.
Jones et al. (2001) "RNA-directed transcriptional gene silencing in plants can be inherited independently of the RNA trigger and requires Met1 for maintenance" *Curr. Biol.* 11(10) 747-757.
Jopling et al. (2005) "Modulation of Hepatitis C Virus RNA Abundance by a Liver-Specific MicroRNA" *Science* 309(5740):1577-1581.
Kawasaki et al. (2004) "Induction of DNA methylation and gene silencing by short interfering RNAs in human cells" *Nature* 431:211-7.
Ketting et al. (2001) "Dicer functions in RNA interference and in synthesis of small RNA involved in developmental timing in C. elegans" *Genes Dev.* 15:2654-2659.
Kim et al. (2000) "E-cadherin-mediated Cell-Cell Attachment Activates Cdc42" *Journal of Biological Chemistry* 275(47):36999-37005.
Kuwabara et al. (2004) "A Small Modulatory dsRNA Specifies the Fate of Adult Neural Stem Cells" *Cell* 116(6):779-793.

(Continued)

*Primary Examiner* — Dana Shin
(74) *Attorney, Agent, or Firm* — Edward J. Baba; Shweta Chandra; Bozicevic, Field & Francis LLP

(57) ABSTRACT

The present invention provides compositions, pharmaceutical preparations, kits and methods for increasing expression of a gene product in a cell by contacting the cell with a small activating RNA (saRNA) molecule comprising a ribonucleic strand that is complementary to a non-coding nucleic acid sequence of the gene.

7 Claims, 21 Drawing Sheets

(56) References Cited

OTHER PUBLICATIONS

Lee et al. (2002) "Expression of small interfering RNAs targeted against HIV-1 rev transcripts in human cells" *Nature Biotechnology* 20:500-505.

Li and Dahiya (2002) "Methprimer: designing primers for methylation PCRs," *Bioinformatics* 18(11):1427-1431.

Li et al. (2000) "Frequent Methylation of Estrogen Receptor in Prostate Cancer: Correlation with Tumor Progression" *Cancer Res* 60:702-706.

Li et al. (2005) "Small interfering RNA directed transcriptional activation in human cells" *American Assn for Cancer Research, Proceedings of the Annual Mtg* 46(Abstract #6105):1436.

Li et al. (2006) "Small dsRNAs induce transcriptional activation in human cells" *PNAS* 103(46):17337-17342.

Liu et al. (2004) "Argonaute2 is the Catalytic Engine of Mammalian RNAi," *Science* 305:1437-1441.

Martinez et al. (2002) "Single-Stranded Antisense siRNAs Guide Target RNA Cleavage in RNAi" *Cell* (110)5:563-574.

Mette et al. (2000) "Transcriptional silencing and promoter methylation triggered by double-stranded RNA" *Embo J* 19:5194-201.

Miyagishi and Taira (2002) "U6 promoter—driven siRNAs with four uridine 3' overhangs efficiently suppress targeted gene expression in mammalian cells" *Nature Biotechnology* 20:497-500.

Morris et al. (2004) "Small Interfering RNA-Induced Transcriptional Gene Silencing in Human Cells" *Science* 305:1289-1292.

Nguyen et al. (2002) "Histone H3-Lysine 9 Methylation is Associated with Aberrant Gene Silencing in Cancer Cells and Rapidly Reversed by 5-Aza-2'-deoxycytidine," *Cancer Res* 62:6456-6461.

Novina et al. (2002) "siRNA-directed inhibition of HIV-1 infection," *Nature Medicine* 8:681-686.

Orphanides and Reinberg (2002) "A Unified Theory of Gene Expression" *Cell* 108(4):439-451.

Paddison et al. (2002) "Short hairpin RNAs (shRNAs) induce sequence-specific silencing in mammalian cells" *Genes Dev* 16:948-958.

Paul et al. (2002) "Effective expression of small interfering RNA in human cells" *Nature Biotechnology* 20: 505-508.

Pelissier et al. (1999) "Heavy de novo methylation at symmetrical and non-symmetrical sites is a hallmark of RNA-directed DNA methylation" *Nucleic Acids Res* 27:1625-1634.

Provost et al. (2002) "Ribonuclease activity and RNA binding of recombinant human Dicer" *The EMBO Journal* 21(21):5864-5874.

Reynolds et al. (2004) "Rational siRNA design for RNA interference" *Nat Biotechnol* 22:326-330.

Saffen et al. (1999) "Control elements of muscarinic receptor gene expression" *Life Sciences* 64(6-7):479-486.

Scacheri et al. (2004) "Short interfering RNAs can induce unexpected and divergent changes in the levels of untargeted proteins in mammalian cells" *PNAS* 101(7):1892-1897.

Schramke et al. (2005) "RNA-interference-directed chromatin modification coupled to RNA polymerase II transcription" *Nature* 435(7046):1275-1279.

Shi et al. (2004) "Histone Demethylation Mediated by the Nuclear Amine Oxidase Homolog LSD1" *Cell* 119:941-953.

Sijen et al. (2001) "Transcriptional and posttranscriptional gene silencing are mechanistically related" *Curr Biol* 11:436-440.

Stockinger et al. (2001) "E-cadherin regulates cell growth by modulating proliferation-dependent β-catenin transcriptional activity" *JCB Article* 154(6):1185-96.

Tabara et al. (2002) "The dsRNA Binding Protein RDE-4 Interacts with RDE-1, DCR-1, and a DExH-Box Helicase to Direct RNAi in C. elegans" *Cell* 109(7):861-871.

Tabara et al. (2002) "The dsRNA Binding Protein RDE-4 Interacts with RDE-1, DCR-1, and a DExH-Box Helicase to Direct RNAi in C. elegans" *Cell* 109: 861-871.

Ting et al. (2005) "Short double-stranded RNA incudes transcriptional gene silencing in human cancer cells in the absence of DNA methylation" *Nat Genet* 37(8):906-910.

Toulmé (2001) "New candidates for true antisense" *Nature Biotechnology* 19:17-18.

Tuschl (2002) "Expanding small RNA interference" *Nature Biotechnology* 20:446-448.

Verdel et al. (2004) "RNAi-Mediated Targeting of Heterochromatin by the RITS Complex" *Science* 303:672-676.

Volpe et al. (2002) "Regulation of Heterochromatic Silencing and Histone H3 Lysine-9 Methylation by RNAi" *Science* 297:1833-1837.

Wang et al. (2004) "Human PAD4 Regulates Histone Arginine Methylation Levels via Demethylimination" *Science* 306:279-283.

Zhang (2004) "No exception to reversibility" *Nature* 431:637-639.

* cited by examiner

A.

| | saControl | – | – | + | + | – | – | – | – | – | – |
| | saEcad-P1 | – | – | – | – | + | + | – | – | – | – |
| | saEcad-P2 | – | – | – | – | – | – | + | + | – | – |
| | saEcad-P3 | – | – | – | – | – | – | – | – | + | + |

E-cadherin
Actin
GAPDH

B.

| | saControl | – | – | + | + | – | – | – | – | – | – |
| | saEcad-P1 | – | – | – | – | + | + | – | – | – | – |
| | saEcad-P2 | – | – | – | – | – | – | + | + | – | – |
| | saEcad-P3 | – | – | – | – | – | – | – | – | + | + |

E-cadherin
GAPDH

A.

B.

A.

B.

C.

A.

B.

A.

B.

C.

A.

B.

C.

A. E-cadherin promoter

B. p21 promoter

C. VEGF promoter

D. Model

Potential saRNA target regions

SEQUENCE LISTING

```
<160> NUMBER OF SEQ ID NOS: 78

<210> SEQ ID NO 1
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 1
agaacucagc caaguguaat t                                                    21

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 2
uuacacuugg cugaguucut t                                                    21

<210> SEQ ID NO 3
<211> LENGTH: 26
<212> TYPE: DNA
<213> ORGANISM: Artificial Sequence
<220> FEATURE:
<223> OTHER INFORMATION: synthetic oligonucleotide: RNA molecules with
      T's at positions 25 and 26

<400> SEQUENCE: 3
agaacucagc caaguguaaa agcctt                                               26

<210> SEQ ID NO 4
<211> LENGTH: 26
<212> TYPE: DNA
<213> ORGANISM: Artificial Sequence
<220> FEATURE:
<223> OTHER INFORMATION: synthetic oligonucleotide: RNA molecules with
      T's at positions 25 and 26

<400> SEQUENCE: 4
ggcuuuuaca cuuggcugag uucutt                                               26

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 5
aaccgugcag gucccauaat t                                                    21

<210> SEQ ID NO 6
```

```
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 6
uuaugggacc ugcacgguut t                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 7
aaccgugcag guccuuauct t                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 8
gauaaggacc ugcacgguut t                                              21

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 9
cguaaugcag gucccauaat t                                              21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 10
uuaugggacc ugcauuacgt t                                              21

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide: RNA molecules with
      T's at positions 25 and 26

<400> SEQUENCE: 11
aaccgugcag gucccauaac ccactt                                         26

<210> SEQ ID NO 12
<211> LENGTH: 26
```

```
<212> TYPE: DNA
<213> ORGANISM: Artificial Sequence
<220> FEATURE:
<223> OTHER INFORMATION: synthetic oligonucleotide: RNA molecules with
      T's at positions 25 and 26

<400> SEQUENCE: 12 gugguuaug ggaccugcac gguutt                                           26

<210> SEQ ID NO 13
<211> LENGTH: 16
<212> TYPE: DNA
<213> ORGANISM: Artificial Sequence
<220> FEATURE:
<223> OTHER INFORMATION: synthetic oligonucleotide: RNA molecules with
      T's at positions 15 and 16

<400> SEQUENCE: 13
ugcagguccc auaatt                                                     16

<210> SEQ ID NO 14
<211> LENGTH: 16
<212> TYPE: DNA
<213> ORGANISM: Artificial Sequence
<220> FEATURE:
<223> OTHER INFORMATION: synthetic oligonucleotide: RNA molecules with
      T's at positions 15 and 16

<400> SEQUENCE: 14
uuaugggacc ugcatt                                                     16

<210> SEQ ID NO 15
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 15
gcgguacggg gggcggugcc uccgg                                           25

<210> SEQ ID NO 16
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 16
ggaggcaccg cccccguac cgcug                                            25

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 17
cuagcaacuc caggcuagat t                                               21

<210> SEQ ID NO 18
<211> LENGTH: 21
<212> TYPE: DNA
<213> ORGANISM: Artificial Sequence
<220> FEATURE:
```

```
<223> OTHER INFORMATION: synthetic oligonucleotide: RNA molecules with
      T's at positions 20 and 21

<400> SEQUENCE: 18
ucuagccugg aguugcuagt t                                                   21

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 19
ugaacccuca gccaaucagt t                                                   21

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 20
cugauuggcu gaggguucat t                                                   21

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 21
ucagcgguac gggggcggt t                                                    21

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 22 ccgcccccg uaccgcugat t                                                    21

<210> SEQ ID NO 23
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 23
ccaacucauu cuccaaguat t                                                   21

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide: RNA molecules with
```

```
                            T's at positions 20 and 21

<400> SEQUENCE: 24
uacuuggaga augaguuggt t                                              21

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 25
ccaacucauu cucccguuct t                                              21

<210> SEQ ID NO 26
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 26
gaacgggaga augaguuggt t                                              21

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 27
uguggucauu cuccaaguat t                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 28
uacuuggaga augaccacat t                                              21

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 29
ccaacuuucc auccaaguat t                                              21

<210> SEQ ID NO 30
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21
```

<400> SEQUENCE: 30
uacuuggaug gaaaguuggt t                                            21

<210> SEQ ID NO 31
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 31
gcaacuccag ucccaaauat t                                            21

<210> SEQ ID NO 32
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 32
uauuugggac uggaguugct t                                            21

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 33
acuuacgagu gacaguagat t                                            21

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 34
ucuacuguca cucguaagut t                                            21

<210> SEQ ID NO 35
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 35
acuacugagu gacaguagat t                                            21

<210> SEQ ID NO 36
<211> LENGTH: 21
<212> TYPE: DNA
<213> ORGANISM: Artificial Sequence
<220> FEATURE:
<223> OTHER INFORMATION: synthetic oligonucleotide: RNA molecules with
      T's at positions 20 and 21

<400> SEQUENCE: 36
ucuacuguca cucaguagut t     21

<210> SEQ ID NO 37
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 37
gcacggaagu ccaucugaau u     21

<210> SEQ ID NO 38
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 38
uucagaugga cuuccgugcu u     21

<210> SEQ ID NO 39
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 39
gagaagaggu gcucaagaau u     21

<210> SEQ ID NO 40
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 40
uucuugagca ccucuucucu u     21

<210> SEQ ID NO 41
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 41
gaaauuagca gauugguaau u     21

<210> SEQ ID NO 42
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 42
uuaccaaucu gcuaauuucu u     21

<210> SEQ ID NO 43
<211> LENGTH: 21

```
<212> TYPE: RNA
<213> ORGANISM: Artificial Sequence
<220> FEATURE:
<223> OTHER INFORMATION: synthetic oligonucleotide

<400> SEQUENCE: 43
ggccagaacu aauagcaauu u                                              21

<210> SEQ ID NO 44
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 44
auugcuauua guucuggccu u                                              21

<210> SEQ ID NO 45
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 45
uucuccgaac gugucacguu u                                              21

<210> SEQ ID NO 46
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 46
acgugacacg uucggagaau u                                              21

<210> SEQ ID NO 47
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 47
attttagttt gggtgaaaga gtgag                                          25

<210> SEQ ID NO 48
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 48
aaccctctaa cctaaaatta ctaaaatcta                                     30

<210> SEQ ID NO 49
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 49
```
tttagtaatt ttaggttaga gggttat                                    27

<210> SEQ ID NO 50
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 50
aaactcacaa atactttaca attcc                                      25

<210> SEQ ID NO 51
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 51
ggtgaaagag tgagccccat ctc                                        23

<210> SEQ ID NO 52
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 52
ttcacctgcc ggccacagcc aatca                                      25

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
cagctgcatt gggtaaatcc                                            20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
gacacatttc cccacgaagt                                            20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
cctgggactc cacctacaga                                            20

<210> SEQ ID NO 56
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 56
ggatgacaca gcgtgagaga                                                     20

<210> SEQ ID NO 57
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 57
tcccatcacc atcttcca                                                       18

<210> SEQ ID NO 58
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 58
catcacgcca cagtttcc                                                       18

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
tctacaatga gctgcgtgtg                                                     20

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
atctccttct gcatcctgtc                                                     20

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
gctggaagcc tgtcaaagag                                                     20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
gagctccagg gcatactgag                                                     20
```

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
taccaccagg tgtgcctaca                                               20

<210> SEQ ID NO 64
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
aaagcatggg tggtcatagc                                               20

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
gcccagtgga cagcgagcag                                               20

<210> SEQ ID NO 66
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 66
gccggcgttt ggagtggtag a                                             21

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
cctcaccatc atcacactgg                                               20

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
tctgagtcag gcccttctgt                                               20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 69
cccactgagg agtccaacat                                              20

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 70
aaatgctttc tccgctctga                                              20

<210> SEQ ID NO 71
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 71
gcgaattggg aagagtggta                                              20

<210> SEQ ID NO 72
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 72
gcaggtgctg ggatagagac                                              20

<210> SEQ ID NO 73
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 73
cgcgtccgaa ggctgctcta                                              20

<210> SEQ ID NO 74
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 74
tggctgtgcc ttgtaaaacg ct                                           22

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
atcccagctg gaacaacagt                                              20

<210> SEQ ID NO 76
```

-continued

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 76
gcgtacgtaa gtgtggcaga                                              20

<210> SEQ ID NO 77
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 77
gggtagggaa aagtggcaat                                              20

<210> SEQ ID NO 78
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 78
gagcgagtgc acctcacata                                              20
```

SMALL ACTIVATING RNA MOLECULES AND METHODS OF USE

CROSS-REFERENCE TO RELATED APPLICATIONS

This application is a continuation of U.S. patent application Ser. No. 11/910,722, filed Mar. 10, 2009, now U.S. Pat. No. 8,877,721, which is a 371 of PCT/US2006/013559, filed Apr. 11, 2006, which claims the benefit of earlier-filed U.S. provisional application Ser. No. 60/715,759 filed Sep. 9, 2005, which applications are incorporated herein by reference in their entirety.

GOVERNMENT RIGHTS

This invention was made with government support under federal grant nos. AG021418 and R01 CA101844 awarded by National Institutes of Health. The United States Government has certain rights in this invention.

BACKGROUND OF THE INVENTION

Relatively recent discoveries in the field of RNA metabolism have revealed that the uptake of certain double stranded RNA (dsRNA) can induce a phenomenon known as RNA interference (RNAi). RNAi is a process by which a polynucleotide directly or indirectly inhibits the expression of a gene, e.g., through inhibiting translation of messenger RNA. This phenomenon has been observed in cells of a diverse group of organisms, including *C. elegans, Drosophila*, and humans, providing a powerful therapeutic approach to the genetic control of human disease.

It has been shown that when short RNA duplexes are introduced into mammalian cells in culture, sequence-specific inhibition of target mRNA can be accomplished without inducing an interferon response. These short dsRNAs, referred to as small interfering RNAs (siRNAs), can, for example, act catalytically at sub-molar concentrations to cleave greater than 95% of the target mRNA in a cell. A description of the mechanisms for siRNA activity, as well as some of its applications are described in Provost et al., Ribonuclease Activity and RNA Binding of Recombinant Human Dicer, E.M.B.O.J., 2002 Nov., 1, 21(21): 5864-5874; Tabara et al., The dsRNA Binding Protein RDE-4 Interacts with RDE-1, DCR-1 and a DexH-box Helicase to Direct RNAi in *C. elegans*, Cell, 2002, June 28, 109(7):861-71; Ketting et al., Dicer Functions in RNA Interference and in Synthesis of Small RNA Involved in Developmental Timing in *C. elegans*; and Martinez et al., Single-Stranded Antisense siRNAs Guide Target RNA Cleavage in RNAi, Cell 2002, September 6, 110(5):563.

RNA-induced gene silencing in mammalian cells is presently believed to implicate at least one of three different levels of control: (i) transcription inactivation (siRNA-guided DNA and histone modification, for example, methylation); (ii) siRNA-induced mRNA degradation; and (iii) mRNA-induced transcriptional attenuation. Consequently, the ability to assess gene function via siRNA mediated methods, as well as to develop therapies based on siRNA-induced gene silencing, presents an exciting and valuable tool that will accelerate genome-wide investigations across a broad range of biomedical and biological research. However, application of the technology has been limited to gene silencing and has not been applied to gene activation.

There is accordingly still a need for compounds that can activate gene expression, and methods of using such compounds for the study and treatment of genetic disorders. The present invention addresses these needs, as well as others.

RELEVANT LITERATURE

U.S. Patent Application Publication No. 2004/0224405; Provost et al., E.M.B.O.J., 1, 21(21): 5864-5874 (2002); Tabara et al., Cell, 109(7):861-71 (2002); Martinez et al., Cell 110(5):563 (2002); Mette et al Embo J 19:5194-201 (2000); Sijen T. et al. Curr Biol 11:436-40 (2001); Volpe T. A. et al. Science 297:1833-7 (2002); Morris et al., Science 305:1289-92 (2004); Kawasaki et al., Nature 431:211-7 (2004); Elbashir et al., Methods 26:199-213 (2002); Reynolds et al., Nat Biotechnol 22:326-30 (2004); Pelissier et al., Nucleic Acids Res 27:1625-34 (1999); Ting et al., Nat. Genet. 37(8): 906-10 (2005); Kawasaki et al., Nature 9:431(7005):211-7 (2004), Morris, et al. Science 305(5688):1289-92 (2004); Schramke et al., Nature 435(7046):1275-9 (2005); and Jaenisch et al., Nat Genet. 33 Suppl:245-54 (2003).

SUMMARY OF THE INVENTION

The present invention provides compositions, pharmaceutical preparations, kits and methods for increasing expression of a gene product in a cell by contacting the cell with a small activating RNA (saRNA) molecule comprising a ribonucleic strand that is complementary to a non-coding nucleic acid sequence of the gene.

These and other advantages of the invention will be apparent from the detailed description below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
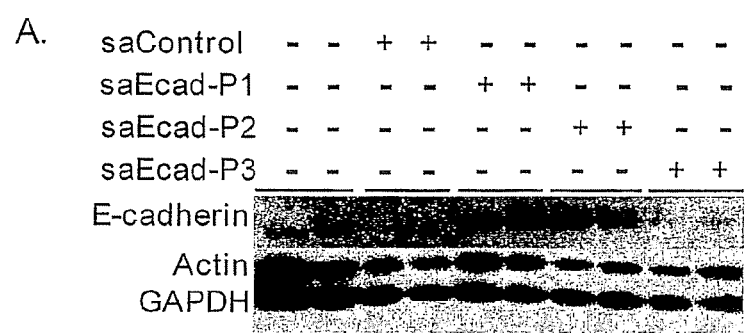
FIG. 1, panel A is a Western blot shows expression of E-cadherin, β-actin and GAPDH in PC-3 cells transfected with 50 nM saRNA for 72 hours. Panel B shows mRNA expression of E-cadherin analyzed by RT-PCR in PC-3 cells transfected as in panel A.
Figure 1:
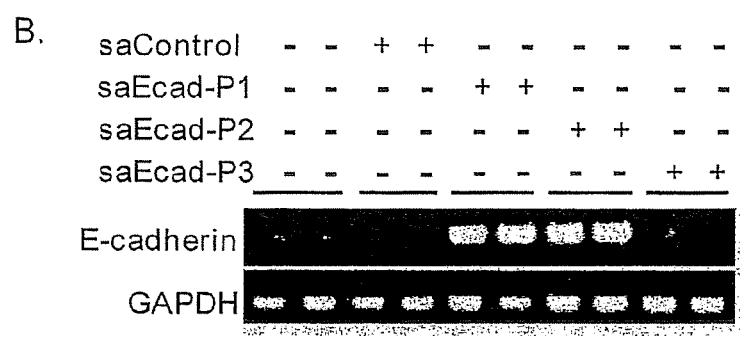

The present invention provides compositions, pharmaceutical preparations, and methods for increasing activity of a gene product through transcriptional activation of the encoding gene in a cell by contacting the cell with a small activating RNA (saRNA) molecule comprising a ribonucleic strand that is complementary to a non-coding nucleic acid sequence of the gene. Also provided are kits for practicing the subject methods of the invention.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a sample" includes a plurality of such samples and reference to "the molecule" includes reference to one or more molecules and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

As used herein the term "isolated" is meant to describe a compound of interest (e.g., either a polynucleotide or a polypeptide) that is in an environment different from that in which the compound might naturally occur.

"Purified" as used herein refers to a compound removed from an environment in which it was produced and is at least 60% free, preferably 75% free, and most preferably 90% free from other components with which it is naturally associated or with which it was otherwise associated with during production.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes."

Perfect complementarity or 100% complementarity refers to the situation in which each nucleotide unit of one polynucleotide strand can hydrogen bond with a nucleotide unit of a second polynucleotide strand, without a "mismatch". Less than perfect complementarity refers to the situation in which not all nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. Substantial complementarity refers to about 79%, about 80%, about 85%, about 90%, about 95%, or greater complementarity. Thus, for example, two polynucleotides of 29 nucleotide units each, wherein each comprises a di-dT at the 3' terminus such that the duplex region spans 27 bases, and wherein 26 of the 27 bases of the duplex region on each strand are complementary, are substantially complementary since they are 96.3% complementary when excluding the di-dT overhangs. In determining complementarity, overhang regions are excluded.

The term "conjugate" refers to a polynucleotide that is covalently or non-covalently associated with a molecule or moiety that alters the physical properties of the polynucleotide such as increasing stability and/or facilitate cellular uptake of double stranded RNA by itself. A "terminal conjugate" may have a molecule or moiety attached directly or indirectly through a linker to a 3' and/or 5' end of a polynucleotide or double stranded polynucleotide. An internal conjugate may have a molecule or moiety attached directly or indirectly through a linker to a base, to the 2' position of the ribose, or to other positions that do not interfere with Watson-Crick base pairing, for example, 5-aminoallyl uridine.

In a double stranded polynucleotide, one or both 5' ends of the strands of polynucleotides comprising the double stranded polynucleotide can bear a conjugated molecule or moiety, and/or one or both 3' ends of the strands of polynucleotides comprising the double stranded polynucleotide can bear a conjugated molecule or moiety.

Conjugates may contain, for example, amino acids, peptides, polypeptides, proteins, antibodies, antigens, toxins, hoiniones, lipids, nucleotides, nucleosides, sugars, carbohydrates, polymers such as polyethylene glycol and polypropylene glycol, as well as analogs or derivatives of all of these classes of substances. Additional examples of conjugates are steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecandiol or undecyl groups, phospholipids such as di-hexadecyl-rac-glycerol, triethylammonium 1,2-di-O-hexadecyl-rac-glycer-o-3-H-phosphonate, polyamines, polyethylene glycol, adamantane acetic acid, palmityl moieties, octadecylamine moieties, hexylaminocarbonyl-oxyc-holesterol, farnesyl, geranyl and geranylgeranyl moieties.

Conjugates can also comprise a detectable label. For example, conjugates can be a polynucleotide covalently attached to a fluorophore. Conjugates may include fluorophores such as TAMRA, BODIPY, Cyanine derivatives such as Cy3 or Cy5, Dabsyl, or any other suitable fluorophore known in the art.

A conjugate molecule or moiety may be attached to any position on the terminal nucleotide that is convenient and that does not substantially interfere with the desired activity of the polynucleotide(s) that bear it, for example the 3' or 5' position of a ribosyl sugar. A conjugate molecule or moiety substantially interferes with the desired activity of an saRNA if it adversely affects its functionality such that the ability of the saRNA to mediate gene activation is reduced by greater than 80% in an in vitro assay employing cultured cells, where the functionality is measured at 24 hours post transfection.

The phrase or "effective concentration" refers to a concentration of saRNA in a cell effective to cause an increase in transcription of a gene of interest in the cell. Of particular interest is an effective concentration that provides a greater than or equal to at least about 45% or more increase, including about 50% or more, about 60% or more, about 70% or more, about 75% or more, about 80% or more increase in target sequence activity relative to a basal expression level, at levels of about 10 nM at 24, 48, 72, and 96 hours following administration, with concentrations of saRNA that provide for a greater than or equal to at least about 25% or more increase, including about 30% or more, about 35% or more, about 40% increase of target sequence activity at about 10 nM at 24 hours following administration also being considered effective, although of less interest. Target sequence activity may be measured by any method known in the art. For example, where the target sequence is a promoter, target sequence activity may be measured by level of transcription, level of the protein whose transcription is operably linked or operably associated with the promoter, or activity of the protein whose transcription is operably linked or operably associated with the promoter.

The term "polynucleotide" refers to polymers of nucleotides, and includes but is not limited to single stranded or double stranded molecule of DNA, RNA, or DNA/RNA hybrids including polynucleotide chains of regularly and irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides wherein the substitution or attachment of various entities or moieties to the nucleotide units at any position, as well as naturally-occurring or non-naturally occurring backbones, are included.

The term "polyribonucleotide" refers to a polynucleotide comprising two or more modified or unmodified ribonucleotides and/or their analogs.

The term "ribonucleotide" and the phrase "ribonucleic acid" (RNA), refer to a naturally occurring or non-naturally occurring (artificial, synthetic), modified or unmodified nucleotide or polynucleotide. A ribonucleotide unit comprises an oxygen attached to the 2' position of a ribosyl moiety that has a nitrogenous base attached in N-glycosidic linkage at the 1' position of a ribosyl moiety, and a moiety that either allows for linkage to another nucleotide or precludes linkage. "Ribonucleic acid" as used herein can have a naturally occurring or modified phosphate backbone (e.g., as produced by synthetic techniques), and can include naturally-occurring or non-naturally-occurring, genetically encodable or non-genetically encodable, residues.

The term "deoxyribonucleotide" refers to a nucleotide or polynucleotide lacking an OH group at the 2' and/or 3' position of a sugar moiety. Instead it has a hydrogen bonded to the 2' and/or 3' carbon. Within an saRNA molecule that comprises one or more deoxyribonucleotides, "deoxyribonucleotide" refers to the lack of an OH group at the 2' position of the sugar moiety, having instead a hydrogen bonded directly to the 2' carbon. "Deoxyribonucleic acid" as used herein can have a naturally occurring or modified phosphate backbone (e.g., as produced by synthetic techniques), and can include naturally-occurring or non-naturally-occurring, genetically encodable or non-genetically encodable, residues.

The term "gene" as used herein includes sequences of nucleic acids that when present in an appropriate host cell facilitates production of a gene product. "Genes" can include nucleic acid sequences that encode proteins, and sequences that do not encode proteins, and includes genes that are endogenous to a host cell or are completely or partially recombinant (e.g., due to introduction of a exogenous polynucleotide encoding a promoter and a coding sequence, or introduction of a heterologous promoter adjacent an endogenous coding sequence, into a host cell). For example, the term "gene" includes nucleic acid that can be composed of exons and introns. Sequences that code for proteins are, for example, sequences that are contained within exons in an open reading frame between a start codon and a stop codon, "Gene" as used herein can refer to a nucleic acid that includes, for example, regulatory sequences such as promoters, enhancers and all other sequences known in the art that control the transcription, expression, or activity of another gene, whether the other gene comprises coding sequences or non-coding sequences. In one context, for example, "gene" may be used to describe a functional nucleic acid comprising regulatory sequences such as promoter or enhancer. The expression of a recombinant gene may be controlled by one or more heterologous regulatory sequences. "Heterologous" refers to two elements that are not normally associated in nature.

A "target gene" is a nucleic acid containing a sequence, such as, for example, a promoter or enhancer, against which an saRNA can be directed for the purpose of effectuating activation of expression. Either or both "gene" and "target gene" may be nucleic acid sequences naturally occurring in an organism, transgenes, viral or bacterial sequences, chromosomal or extrachromosomal, and/or transiently or chronically transfected or incorporated into the cell and/or its chromatin. A "target gene" can, upon saRNA-mediated activation, repress the activity of another "gene" such as a gene coding for a protein (as measured by transcription, translation, expression, or presence or activity of the gene's protein product). In another example, a "target gene" can comprise an enhancer, and saRNA mediated activation of the enhancer may increase the functionality of an operably linked or operably associated promoter, and thus increase the activity of another "gene" such as a gene coding for a protein that is operably linked to the increased promoter and/or enhancer.

"Regulatory elements" are nucleic acid sequences that regulate, induce, repress, or otherwise mediate the transcription, translation of a protein or RNA coded by a nucleic acid sequence with which they are operably linked or operably associated. Typically, a regulatory element or sequence such as, for example, an enhancer or repressor sequence, is operatively linked or operatively associated with a protein or RNA coding nucleic acid sequence if the regulatory element or regulatory sequence mediates the level of transcription, translation or expression of the protein coding nucleic acid sequence in response to the presence or absence of one or more regulatory factors that control transcription, translation and/or expression. Regulatory factors include, for example, transcription factors. Regulatory sequences may be found in introns.

Regulatory sequences or element include, for example, "TATAA" boxes, "CAAT" boxes, differentiation-specific elements, cAMP binding protein response elements, sterol regulatory elements, serum response elements, glucocorticoid response elements, transcription factor binding elements such as, for example, SPI binding elements, and the like. A "CAAT" box is typically located upstream (in the 5' direction) from the start codon of a eukaryotic nucleic acid sequence encoding a protein or RNA. Examples of other regulatory sequences include splicing signals, polyadenylation signals, termination signals, and the like. Further examples of nucleic acid sequences that comprise regulatory sequences include the long terminal repeats of the Rous sarcoma virus and other retroviruses. An example of a regulatory sequence that controls tissue-specific transcription is the interferon-epsilon regulatory sequence that preferentially induces production of the operably linked sequence encoding the protein in placental, tracheal, and uterine tissues, as opposed to lung, brain, liver, kidney, spleen, thymus, prostate, testis, ovary, small intestine, and pancreatic tissues. Many, many regulatory sequences are known in the art, and the foregoing is merely illustrative of a few.

The term "enhancer" and phrase "enhancer sequence" refer to a variety of regulatory sequence that can increase the efficiency of transcription, without regard to the orientation of the enhancer sequence or its distance or position in space from the promoter, transcription start site, or first codon of the nucleic acid sequence encoding a protein with which the enhancer is operably linked or associated.

The term "promoter" refers to a nucleic acid sequence that does not code for a protein, and that is operably linked or operably associated to a protein coding or RNA coding nucleic acid sequence such that the transcription of the operably linked or operably associated protein coding or RNA coding nucleic acid sequence is controlled by the promoter. Typically, eukaryotic promoters comprise between 100 and 5,000 base pairs, although this length range is not meant to be limiting with respect to the term "promoter" as used herein. Although typically found 5' to the protein coding nucleic acid sequence to which they are operably linked or operably associated, promoters can be found in intron sequences as well.

The term "promoter" is meant to include regulatory sequences operably linked or operably associated with the same protein or RNA encoding sequence that is operably linked or operably associated with the promoter. Promoters can comprise many elements, including regulatory elements.

The term "promoter" comprises promoters that are inducible, wherein the transcription of the operably linked nucleic acid sequence encoding the protein is increased in response to an inducing agent. The term "promoter" may also comprise promoters that are constitutive, or not regulated by an inducing agent.

The phrases "operably associated" and "operably linked" refer to functionally related nucleic acid sequences. By way of example, a regulatory sequence is operably linked or operably associated with a protein encoding nucleic acid sequence if the regulatory sequence can exert an effect on the expression of the encoded protein. In another example, a promoter is operably linked or operably associated with a protein encoding nucleic acid sequence if the promoter controls the transcription of the encoded protein. While operably associated or operably linked nucleic acid sequences can be contiguous with the nucleic acid sequence that they control, the phrases "operably associated" and "operably linked" are not meant to be limited to those situations in which the regulatory sequences are contiguous with the nucleic acid sequences they control.

The phrase "non-coding target sequence" or "non-coding nucleic acid sequence" refers to a nucleic acid sequence of interest that is not contained within an exon or is a regulatory sequence.

The term "nucleotide" refers to a ribonucleotide or a deoxyribonucleotide or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

"Nucleotide analogs" include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

"Modified bases" refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. The term "nucleotide" is also meant to include the NT to P5' phosphoramidate, resulting from the substitution of a ribosyl 3' oxygen with an amine group.

Further, the term "nucleotide" also includes those species that have a detectable label, such as for example a radioactive or fluorescent moiety, or mass label attached to the nucleotide.

The phrase "nucleotide unit" refers to a single nucleotide residue and is comprised of a modified or unmodified nitrogenous base, a modified or unmodified sugar, and a modified or unmodified moiety that allows for linking of two nucleotides together or a nucleotide to a conjugate that precludes further linkage. The single nucleotide residue may be in a polynucleotide. Thus, a polynucleotide having 27 bases has 27 nucleotide units.

The phrase "nuclear uptake enhancing modification" refers to a modification of a naturally occurring or non-naturally occurring polynucleotide that provides for enhanced nuclear uptake. An example of a "nuclear uptake enhancing modification" is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus. An effective concentration is a concentration that results in a detectable change in the transcription or activity of a gene or target sequence as the result of the accumulation of nucleic acid within the nucleus.

The phrases "orthoester protected" and "orthoester modified" refer to modification of a sugar moiety within a nucleotide unit with an orthoester. Preferably, the sugar moiety is a ribosyl moiety. In general, orthoesters have the structure RC(OR')$_3$ wherein each R' can be the same or different, R can be an H, and wherein the underscored C is the central carbon of the orthoester. The orthoesters of the present invention are comprised of orthoesters wherein a carbon of a sugar moiety in a nucleotide unit is bonded to an oxygen, which is in turn bonded to the central carbon of the orthoester. To the central carbon of the orthoester is, in turn, bonded two oxygens, such that in total three oxygens bond to the central carbon of the orthoester. These two oxygens bonded to the central carbon (neither of which is bonded to the carbon of the sugar moiety) in turn, bond to carbon atoms that comprise two moieties that can be the same or different. For example, one of the oxygens can be bound to an ethyl moiety, and the other to an isopropyl moiety. In one example, R can be an H, one R' can be a ribosyl moiety, and the other two R' moieties can be 2-ethyl-hydroxyl moieties. Orthoesters can be placed at any position on the sugar moiety, such as, for example, on the 2', 3' and/or 5' positions. Exemplary orthoesters, and methods of making orthoester protected polynucleotides, are described in U.S. Pat. Nos. 5,889,136 and 6,008,400, each herein incorporated by reference in its entirety.

The term "stabilized" refers to the ability of a dsRNA to resist degradation while maintaining functionality and can be measured in terms of its half-life in the presence of, for example, biological materials such as serum. The half-life of an saRNA or an siRNA in, for example, serum refers to the time taken for the 50% of saRNA or siRNA to be degraded.

The phrase "duplex region" refers to the region in two complementary or substantially complementary polynucleotides that form base pairs with one another, either by Watson-Crick base pairing or any other manner that allows for a duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity generally refers to about at least 79%, about 80%, about 85%, about 85%, about 90%, about 95% or greater complementarity. For example, a mismatch in a duplex region consisting of 19 base pairs (i.e., 18 base pairs and one mismatch) results in about 94.7% complementarity, rendering the duplex region substantially complementary. In another example, three mismatches in a duplex region consisting of 19 base pairs (i.e., 16 base pairs and three mismatches) results in about 84.2% complementarity, rendering the duplex region substantially complementary, and so on.

The term "overhang" refers to a terminal (5' or 3') non-base pairing nucleotide resulting from one strand extending beyond the other strand within a doubled stranded polynucleotide. One or both of two polynucleotides that are capable of forming a duplex through hydrogen bonding of base pairs may have a 5' and/or 3' end that extends beyond the 3' and/or 5' end of complementarity shared by the two polynucleotides. The single-stranded region extending beyond the 3' and/or 5' end of the duplex is referred to as an overhang.

The phrase "gene silencing" refers to the reduction in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. "Gene silencing" refers to the reduction or amelioration of activity associated with a nucleic acid sequence, such as its ability to function as a regulatory sequence, its ability to be transcribed, its ability to be translated and result in expression of a protein, regardless of the mechanism whereby such silencing occurs.

As used herein, the terms "gene activating", "activating a gene", or "gene activation" are interchangeable and refer to an increase in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. Furthermore, "gene activating", "activating a gene", or "gene activation" refer to the increase of activity associated with a nucleic acid sequence, such as its ability to function as a regulatory sequence, its ability to be transcribed, its ability to be translated and result in expression of a protein, regardless of the mechanism whereby such activation occurs.

The phrase "RNA interference" and the term "RNAi" refer to the process by which a polynucleotide or double stranded polynucleotide comprising at least one ribonucleotide unit exerts an effect on a biological process through disruption of gene expression. The process includes but is not limited to gene silencing by degrading mRNA, interactions with tRNA, rRNA, hnRNA, cDNA and genomic DNA, as well as methylation of DNA and ancillary proteins.

The term "siRNA" and the phrase "short interfering RNA" refer to a double stranded nucleic acid that is capable of performing RNAi and that is between 18 and 30 base pairs in length (i.e., a duplex region of between 18 and 30 base pairs). Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides. In contrast, the saRNAs of the invention are distinct from, and thus are not, siRNAs. saRNAs do not facilitate RNAi or gene silencing.

siRNAs can be duplexes, and can also comprise short hairpin RNAs, RNAs with loops as long as, for example, 4 to 23 or more nucleotides, RNAs with stem loop bulges, microRNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms.

The term "histone" refers to a type of protein that is found in the nucleus of eukaryotic cells. The class of proteins referred to as histones are those proteins around which DNA coils in order to compact itself.

The phrase "mammalian cell" refers to a cell of any mammal, including humans. The phrase refers to cells in vivo, such as, for example, in an organism or in an organ of an organism. The phrase also refers to cells in vitro, such as, for example, cells maintained in cell culture.

The term "methylation" refers to the attachment of a methyl group (—CH$_3$) to another molecule. Typically, when DNA undergoes methylation, a methyl group is added to a cytosine bearing nucleotide, commonly at a CpG sequence, although methylation can occur at other sites as well. Proteins, such as, for example, histone 3, may also be methylated at a lysine, e.g., lysine 9.

The term "demethylation" refers to the removal of a methyl group ($-CH_3$) from another molecule. Typically, when DNA undergoes demethylation, a methyl group is removed from a cytosine bearing nucleotide, commonly at a CpG sequence, although demethylation can occur at other sites as well. Proteins, such as, for example, histone 3, may also be demethylated at a lysine, e.g., lysine 9.

The phrase "pharmaceutically acceptable carrier" refers to compositions that facilitate the introduction of dsRNA into a cell and includes but is not limited to solvents or dispersants, coatings, anti-infective agents, isotonic agents, agents that mediate absorption time or release of the inventive polynucleotides and double stranded polynucleotides. Examples of "pharmaceutically acceptable carriers" include liposomes that can be neutral or cationic, can also comprise molecules such as chloroquine and 1,2-dioleoyl-sn-glycero-3-phosphatidylethanolamine, which can help destabilize endosomes and thereby aid in delivery of liposome contents into a cell, including a cell's nucleus. Examples of other pharmaceutically acceptable carriers include poly-L-lysine, polyalkylcyanoacrylate nanoparticles, polyethyleneimines, and any suitable PAMAM dendrimers (polyamidoamine) known in the art with various cores such as, for example, ethylenediamine cores, and various surface functional groups such as, for example, cationic and anionic functional groups, amines, ethanolamines, aminodecyl.

Overview

The present invention provides methods and compositions for activation of a gene by introducing in the nucleus of a cell at least one small activating RNA (saRNA) molecule, wherein the saRNA molecule comprises a first ribonucleic acid strand comprising a ribonucleotide sequence complementary to a non-coding nucleic acid sequence of the gene, wherein this region of complementarity is selected so as to provide for an increase in transcription of the corresponding gene, and usually at least two terminal residues at the 3' end which are not complementary to the non-coding sequence (e.g., dTdT). The region of complementarity is usually more than about 14 residues and less than 30, usually less than 26 nucleotides. The saRNA can be provided as a double-stranded molecule, with a second strand complementary to the first strand and forming a duplex region with the first strand, usually with at least a two residue overhang at the 3' ends of each of the first and second strands. The saRNA can also be provided as a single stranded molecule that forms a double-stranded region, wherein the first region comprising a ribonucleotide sequence complementary to a non-coding nucleic acid sequence of the gene, and a second region comprises a ribonucleotide sequence complementary to the first region and forming a duplex region with the first region, usually with at least a two residue overhang at the 3' ends of the strand.

This invention is based in part on the surprising discovery that introduction of a saRNA molecule into a cell effects sequence specific transcriptional activation in mammalian cells. Furthermore, a novel mechanism for gene activation was established from cell culture studies.

As described in the examples in more detail, the invention is based on the discovery that saRNAs targeting the E-cadherin promoter, p21 promoter, or VEGF promoter, induce E-cadherin mRNA and protein expression in human cells, p21 mRNA expression and protein expression in human cells, or VEGF mRNA and protein expression in human cells, respectively. Mechanistically, and without wishing to be bound to theory, saRNA-directed transcriptional activation (RdTA) is associated with decreased histone methylation (e.g., histone 3, which was observed to be at a lysine residue (e.g., lysine residue 9)), and mediated by Ago2 protein. These observations support a fundamental role for saRNA in regulating genome structure and function and identify a therapeutic use for saRNA in targeted gene activation (e.g., increasing gene expression).

In one aspect the invention provides methods of increasing expression of a gene (i.e., gene activation) by introducing a saRNA molecule into a mammalian cell (which can be accomplished by delivery of the saRNA into the cell directly or as a result of expression from a DNA introduced into the cell), wherein the saRNA molecule has a strand that is complementary to a region of a non-coding nucleic acid sequence of the gene, wherein the introduction results in an increase in expression of the gene. Increasing gene activity can be useful in the context of a tumor suppressor gene in, for example, inhibition of cellular proliferation, inhibition of cellular transformation and inhibition of cellular migration (e.g., as an anti-cancer agent). In another aspect the invention provides compositions and pharmaceutical preparations comprising at least one saRNA molecules.

The invention will now be described in more detail.

Compositions

As noted above the present invention provides short activating RNA (saRNA) molecules for use in performing gene activation (e.g., increase gene expression) in mammalian cells by targeting a region of non-coding nucleic acid sequence of the gene (e.g., a regulatory sequence).

As used herein the term "saRNA" and the phrase "short activating RNA" refer to a ribonucleic acid molecule capable of facilitating gene activation and can be composed of a first ribonucleic acid strand comprising a ribonucleotide sequence complementary to a non-coding nucleic acid sequence of a gene and a second ribonucleic acid strand comprising a nucleotide sequence complementary to the first strand, wherein the first and second strands form a duplex region. The saRNA can also be composed of as a single strand RNA molecule that forms a double-stranded region, wherein the first region comprising a ribonucleotide sequence complementary to a non-coding nucleic acid sequence of the gene, and a second region comprising a ribonucleotide sequence complementary to the first region and forming a duplex region with the first region. The duplex region of an saRNA molecule is usually between about 10 and about 50 base pairs in length, about 12 and about 48 base pairs, about 14 and about 46 base pairs, about 16 and about 44 base pairs, about 18 and about 42 base pairs, about 20 and about 40 base pairs, about 22 and about 38 base pairs, about 24 and about 36 base pairs, about 26 and about 34 base pairs, about 28 and about 32 base pairs, normally about 10, about, 15, about 20, about 25, about 30, about 35, about 40, about 45, about 50 base pairs in length. Additionally, the term saRNA and the phrase "small activating RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

As used herein, the terms "gene activating", "activating a gene", or "gene activation" are interchangeable and refer to increasing gene expression with respect to transcription as measured by transcription level, mRNA level, enzymatic activity, methylation state, chromatin state or configuration, or other measure of its activity or state in a cell or biological system. Furthermore, "gene activating", "activating a gene", or "gene activation" refer to the increase of activity known to be associated with a nucleic acid sequence, such as its ability to function as a regulatory sequence, its ability to be transcribed, its ability to be translated and result in expression of a protein, regardless of the mechanism whereby such activation occurs.

saRNAs compounds of the present invention can be duplexes, and can be composed of separate strands or can comprise of a single strand of RNA that forms short hairpin RNAs, RNAs with loops as long as, for example, about 4 to about 23 or more nucleotides, about 5 to about 22, about 6 to about 21, about 7 to about 20, about 8 to about 19, about 9 to about 18, about 10 to about 17, about 11 to about 16, about 12 to about 15, about 13 to about 14 nucleotides, RNAs with stem loop bulges, and short temporal RNAs. RNAs having loops or hairpin loops can include structures where the loops are connected to the stem by linkers such as flexible linkers. Flexible linkers can be selected of a wide variety of chemical structures, as long as they are of sufficient length and materials to enable effective intramolecular hybridization of the stem elements. Typically, the length to be spanned is at least about 10-24 atoms. In some embodiments, the saRNA molecules are separate strands, e.g., two different strands that are not covalently linked.

The saRNA molecules of the present invention include a region of complementarity to a non-coding region of appropriate length to provide for transcriptional activation of an adjacent coding sequence. saRNA molecules also typically include 3' terminal nucleotides which are not complementary to the non-coding sequence. saRNA typically comprise more than 10 nucleotides and less than 50 nucleotides, usually more than about 12 nucleotides and less than 48 nucleotides in length, such as about 14 nucleotides to about 46 nucleotides in length, about 16 nucleotides to about 44 nucleotides in length, including about 18 nucleotides to about 42 nucleotides in length, about 20 nucleotides to about 40 nucleotides in length. about 22 nucleotides to about 38 nucleotides in length, about 24 nucleotides to about 36 nucleotides in length, about 26 nucleotides to about 34 nucleotides in length, about 28 nucleotides to about 32 nucleotides in length. In representative embodiments, the saRNA molecules comprise of about 14 nucleotides to about 30 nucleotides in length, such as about 15 nucleotides to about 29 nucleotides in length, about 16 nucleotides to about 28 nucleotides in length, including about 17 nucleotides to about 27 nucleotides in length, about 18 nucleotides to about 26 nucleotides in length, about 19 nucleotides to about 25 nucleotides in length, about 20 nucleotides to about 24 nucleotides in length, about 21 nucleotides to about 23 nucleotides in length, or about 22 nucleotides in length.

The saRNA molecules of the present invention in double-stranded form typically comprises a region of complementarity greater than about 10 base pairs and less than about 50 base pairs in length. In some embodiments, the saRNA molecules comprise a duplex region of between about 12 base pairs to about 48 base pairs in length, such as about 14 base pairs to about 46 base pairs in length, about 16 base pairs to about 44 base pairs in length, including about 18 base pairs to about 42 base pairs in length, about 20 base pairs to about 40 base pairs in length. about 22 base pairs to about 38 base pairs in length, about 24 base pairs to about 36 base pairs in length, about 26 base pairs to about 34 base pairs in length, about 28 base pairs to about 32 base pairs in length. In representative embodiments, the saRNA molecules comprise of a duplex region between about 15 base pairs to about 30 base pairs in length, such as about 16 base pairs to about 29 base pairs in length, about 17 base pairs to about 28 base pairs in length, including about 18 base pairs to about 27 base pairs in length, about 19 base pairs to about 26 base pairs in length, about 20 base pairs to about 25 base pairs in length, about 21 base pairs to about 24 base pairs in length, about 22 base pairs to about 23 base pairs in length.

For example, saRNA for activation of a human E-cadherin gene, as described in the Examples below, includes a 19 nucleotides region of complementarity to a non-coding region of E-cadherin and two 3' terminal dTs, making the saRNA 21 nucleotides in length overall.

In representative embodiments, the saRNA molecules comprise a strand that is complementary to a portion of a non-coding nucleic acid sequence or a gene, e.g., a regulatory sequence, such as a promoter. In some embodiments, the strand is 100% complementary to the non-coding nucleic acid sequence of the gene, including about 99% complementary, 98% complementary, 97% complementary, 96% complementary, 95% complementary, 94% complementary, 93% complementary, 92% complementary, 91% complementary, 90% complementary, 85% complementary, 80% complementary, 75% complementary, 70% complementary to the non-coding nucleic acid sequence of the gene.

As described in greater detail above, the saRNA molecules of the present invention comprises a strand that is complementary to a portion of a non-coding nucleic acid sequence or a gene, e.g., a regulatory sequence, such as a promoter. When designing the complementary strand of the saRNA molecules of the invention (e.g., the strand of the saRNA molecule that is complementary to a portion of a non-coding nucleic acid sequence or a gene), the sequence is selected so as to avoid complementarity to any CpG island regions. By "CpG island region" is meant any region of the nucleic acid that is rich in the dinucleotide "CG" (Cytosine-Guanine). Methylation of the cytosine in the dinucleotide is maintained through cell divisions and affects the degree of transcription of the nearby genes by silencing gene expression and is important in developmental regulation of gene expression. Without being held to theory, avoiding CpG islands serves to avoid methylation of the cytosine residue of CpG island regions and thereby silencing expression of the nearby gene.

In addition, when designing the complementary strand of the saRNA molecules of the invention (e.g., the strand of the saRNA molecule that is complementary to a portion of a non-coding nucleic acid sequence or a gene), the sequence is selected so as to avoid complementarity to any GC-rich regions. By "GC-rich" is meant any region of the nucleic acid that includes a greater number of guanine and cytosine base pairs compared to thymine and adenine base pairs as compared to the average number of guanine and cytosine residues in the rest of the genome in which the nucleic acid is present.

A CpG island region or a GC-rich region can be determined, for example, by using a prediction protocol, such as for example the CpGPlot/CpGReport/Isochore protocol available on the world wide web at ebi.ac.uk/emboss/cpgplot/ or the MethPrimer protocol available on the world wide web at urogene.org/methprimer/index1.html.

Furthermore, the strand of the saRNA molecule that is complementary to a portion of a non-coding nucleic acid sequence or a gene generally tolerates a lower degree of complementarity to the target sequence at its 5' end region as compared to its 3' end region. In other words, the saRNA molecules of the subject invention will typically be designed such that the strand of the saRNA molecule that is complementary to a non-coding nucleic acid sequence has a higher degree of complementarity at its 3' end, preferably perfect complementarity, as compared to its 5' end, which in contrast can tolerate mismatches. Generally, and without being held to theory, the 3' end region includes the region of complementarity, and further the 3' terminus of the region of complementarity and the 3' terminus of the saRNA can be the same (i.e., the 3' terminus of the region of complementarity is defined by the 3' terminus of the saRNA).

By 3' end region is meant the portion of the ribonucleotide strand that includes at least about 10, 11, 12, 13, or 14 nucleotides from the 3' terminus of the saRNA molecule, but will generally not include more than half of the nucleotides of the molecule. In some embodiments the 3' end of the strand of the saRNA molecule that is complementary to a portion of a non-coding nucleic acid sequence is generally 100% complementary to the non-coding nucleic acid sequence, and may be about 99% complementary, 98% complementary, 97% complementary, 96% complementary, or 95% complementary.

In addition, the saRNA molecules of the subject invention will typically be designed in order to avoid a non-coding nucleic acid sequence of a gene comprising a GC content greater than about 50% or less than about 30%. In certain embodiments, the saRNA molecules of the subject invention will be designed in order to comprise a GC content greater than about 30% or less than about 50%, including a GC content of about 32%, a GC content of about 34%, a GC content of about 36%, a GC content of about 38%, a GC content of about 40%, a GC content of about 42%, a GC content of about 44%, a GC content of about 46%, a GC content of about 48%, a GC content of about 50%.

Likewise, the saRNA molecules of the subject invention will typically be designed in order comprise an AT content greater than about 50% to less than about 80%. In certain embodiments, the saRNA molecules of the subject invention will be designed in order to comprise an AT content of about 52%, an AT content of about 54%, an AT content of about 56%, an AT content of about 58%, an AT content of about 60%, an AT content of about 62%, an AT content of about 64%, an AT content of about 66%, an AT content of about 68%, an AT content of about 70%, an AT content of about 72%, an AT content of about 74%, an AT content of about 76%, an AT content of about 78%, an AT content of about 80%.

The saRNA molecules of the subject invention will typically be designed in order to avoid a non-coding nucleic acid sequence of a gene comprising nucleotide repeats and low complex sequences, such as a sequence of four or more of the same base in a row, such as for example AAAA or CCCC. Moreover, the saRNA molecules of the subject invention will typically be designed in order to avoid a non-coding nucleic acid sequence of a gene comprising single nucleotide polymorphism (SNP) sites. Without being held to theory, avoiding GC rich regions, repeats, and non-complex sequences serves to avoid "slippage" of the saRNA when duplexed to the target sequence (e.g., a GC-rich sequence may cause the saRNA to anneal to the target in a manner that adversely affects the overall desired region of complementarity with the target).

The saRNA molecules of the present invention include a region of complementarity to non-coding target nucleic acid sequence. A non-coding target nucleic acid sequence refers to a nucleic acid sequence of interest that is not contained within an exon or is a regulatory sequence. In general, such a non-coding target sequence is a nucleic acid sequence approximately 2 kb upstream from the transcriptional start site of the target gene, including up to about 1.9 kb, about 1.8 kb, about 1.7 kb, about 1.6 kb, about 1.5 kb, about 1.4 kb, about 1.3 kb, about 1.2 kb, about 1.1 kb, about 1 kb, about 950 bp, about 900 bp, about 850 bp, about 800 bp, about 750 bp, about 700 bp, about 650 bp, about 600 bp, about 550 bp, about 500 bp, about 450 bp, about 400 bp, about 350 bp, about 300 bp, about 250 bp, about 200 bp, about 150 bp, about 100 bp, about 50 bp, and the like.

Figure 23:
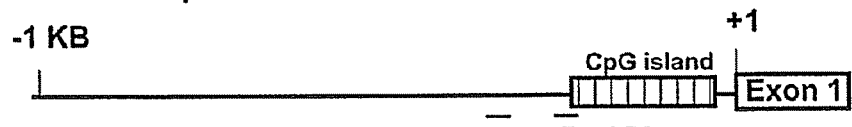
FIG. 23 is a schematic showing the relative locations of regions of complementarity of saRNAs of the invention to target locations of non-coding sequence of a target gene (Panels A-C), and a general model for selection of regions of complementarity of saRNAs for a target gene (Panel D). Panel A shows the complementarity of saRNAs saEcad-P1 and SaEcad-P2 to target locations of non-coding sequence of the E-cadherin gene. Panel B shows the complementarity of the saRNA saP21-322 to the target location of non-coding sequence of the p21 gene. Panel C shows the complementarity of the saRNA saVEGF-607 to the target location of non-coding sequence of the VEGF gene. Panel D shows a general model of exemplary saRNA target regions of a target gene.
Figure 23:
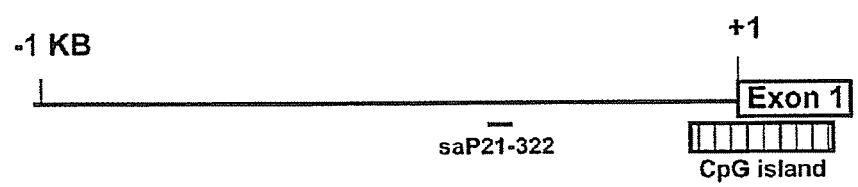
Figure 23:
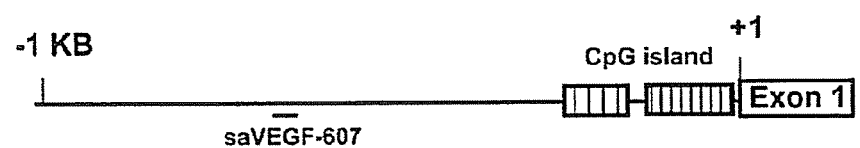
Figure 23:
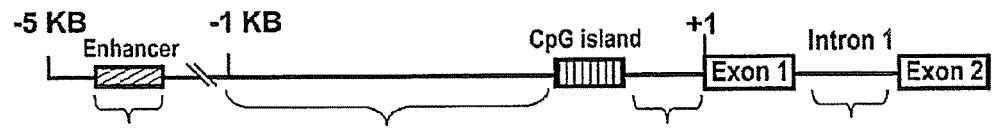

In certain embodiments, the non-coding target nucleic acid sequence may include any enhancer sequence within about a 5 kb region upstream of the transcriptional start site of the target gene, including about 4.5 kb, about 4 kb, about 3.5 kb, about 3 kb, about 2.5 kb, about 2 kb, about 1.5 kb, and the like. In other embodiments, the non-coding target nucleic acid sequence may include the first intron sequence downstream of the transcriptional start site of the target gene. Such target regions are exemplified schematically in FIG. 23, panel D. Exemplary saRNAs with complementarity to target locations of non-coding sequences of target genes are provided in FIG. 23, panel A (E-cadherin), panel B (p21), and panel C (VEGF).

The strands of the saRNA molecule may have terminal (5' or 3') overhang regions of any length that are non-base pairing nucleotide resulting from one strand extending beyond the other strand within a doubled stranded polynucleotide. In addition, the overhang regions are also not complementary (a region of non-complementarity) to the non-coding sequence of the gene. If they have overhang regions, these regions in representative embodiments are 8 nucleotides or fewer in length, 7 nucleotides or fewer in length, 6 nucleotides or fewer in length, including about 5 nucleotides, about 4 nucleotides, such as about 3 nucleotides or fewer in length, including about two nucleotides in length, and about one nucleotide in length. In such embodiments, the regions are further described by the following formula:

$$3'\text{-}N_{(1+n)}\text{-saRNA-5', or}$$

$$5'\text{-}N_{(1+n)}\text{-saRNA-3'}$$

wherein N is any nucleotide, including naturally-occurring or non-naturally-occurring, genetically encodable or non-genetically encodable, residue and n is any integer from 0 to 7.

The nucleotides of the saRNA, or at least one strand of a duplex saRNA, may be modified so as to provide a desired characteristic. For example, the saRNA molecules of the invention can comprise modification of a naturally occurring or non-naturally occurring polynucleotide that provides for enhanced nuclear uptake. An example of a nuclear uptake enhancing modification is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus.

Furthermore, the saRNA can be 2'-O-bis(2-hydroxyethoxy)methyl orthoester modified to provide for stability of the ribonucleic acid molecule. Other modification, include, for example a backbone phosphate group modification (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of the saRNA. Phosphorothioates and phosphorodithioates are more resistant to degradation in vivo than their unmodified oligonucleotide counterparts, increasing the half-lives of the saRNA making them more available to the subject being treated. A saRNA may also be modified to comprise N3'-P5' (NP) phosphoramidate, morpholino phosphorociamidate (MF), locked nucleic acid (LNA), 2'-O-methoxyethyl (MOE), or 2'-fluoro, arabino-nucleic acid (FANA), which can enhance the resistance of the polynucleotide to nuclease degradation (see, e.g., Faria et al. (2001) *Nature Biotechnol.* 19:40-44; Toulme (2001) *Nature Biotechnol.* 19:17-18).

The saRNA may be synthesized by any method that is now known or that comes to be known for synthesizing saRNA molecules and that from reading this disclosure, one skilled in the art would conclude would be useful in connection with the present invention. For example, one may use methods of chemical synthesis such as methods that employ Dharmacon, Inc.'s proprietary ACE® technology. Alternatively, one could also use template dependant synthesis methods. Synthesis may be carried out using modified or non-modified, natural or non-natural bases as disclosed herein. Moreover, synthesis may be carried out with or without modified or non-modified nucleic acid backbone as disclosed herein.

In addition, the saRNA molecules may be synthesized in a host cell by any method that is now known or that comes to be known for synthesizing saRNA molecules in a host cell. For example, saRNA molecules can be expressed from recombinant circular or linear DNA vector using any suitable promoter. Suitable promoters for expressing saRNA molecules of the invention from a vector include, for example, the U6 or H1 RNA pol III promoter sequences and the cytomegalovirus promoter. Selection of other suitable promoters is within the skill in the art. Suitable vectors for use with the subject invention include those described in U.S. Pat. No. 5,624,803, the disclosure of which is incorporated herein in its entirely. The recombinant plasmids of the invention can also comprise inducible or regulatable promoters for expression of the saRNA molecule in a particular tissue or in a particular intracellular environment.

The saRNA molecules of the invention can be expressed from a recombinant nucleic acid vector either as two separate, complementary RNA molecules, or as a single RNA molecule with two complementary regions. Selection of vectors suitable for expressing saRNA of the invention, methods for inserting nucleic acid sequences for expressing the saRNA into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. Other methods for delivery and intracellular expression suitable for use in the invention are described in, for example, U.S. Patent Application Publication Nos. 20040005593, 20050048647, 20050060771, the entire disclosures of which are herein incorporated by reference.

Once synthesized, the polynucleotides of the present invention may immediately be used or be stored for future use. In some embodiments, the polynucleotides of the invention are stored as duplexes in a suitable buffer. Many buffers are known in the art suitable for storing saRNAs. For example, the buffer may be comprised of 100 mM KCl, 30 mM HEPES-pH 7.5, and 1 mM $MgCl_2$. In representative embodiments, the double stranded polynucleotides of the present invention retain 30% to 100% of their activity when stored in such a buffer at 4° C. for one year. More preferably, they retain 80% to 100% of their biological activity when stored in such a buffer at 4° C. for one year. Alternatively, the compositions can be stored at −20° C. in such a buffer for at least a year or more. Usually, storage for a year or more at −20° C. results in less than a 50% decrease in biological activity. More usually, storage for a year or more at −20° C. results in less than a 20% decrease in biological activity after a year or more. Furthermore, storage for a year or more at −20° C. results in less than a 10% decrease in biological activity.

In order to ensure stability of the saRNA prior to usage, they may be retained in dry form (e.g., lyophilized form) at −20° C. until they are ready for use. Prior to usage, they should be resuspended; however, even once resuspended, for example, in the aforementioned buffer, they should be kept at −20° C. until used. The aforementioned buffer, prior to use, may be stored at approximately 4° C. or room temperature. Effective temperatures at which to conduct transfection are well known to persons skilled in the art, but include for example, room temperature.

Methods

The present invention provides methods of increasing gene expression comprising introducing a saRNA molecule into a mammalian cell's nucleus, wherein the saRNA molecule has a strand that is complementary to a region of a non-coding nucleic acid sequence of the gene, wherein the introduction results in an increase in expression of the gene. In general, "increasing gene expression" refers to an increase in the gene's ability to be transcribed, its ability to be translated and result in expression of a protein, regardless of the mechanism whereby such activation occurs.

In general, the methods of the present invention are carried out by contacting a cell with an saRNA molecule, wherein the saRNA molecule comprises a first ribonucleic acid strand comprising a ribonucleotide sequence complementary to a non-coding nucleic acid sequence of a gene and a second ribonucleic acid strand comprising a nucleotide sequence complementary to the first strand, wherein the first and second strands form a duplex region of between about 15 to about 30 base pairs in the saRNA molecule, wherein the introduction results in an increase in expression of the gene.

In representative embodiments, an increase in gene expression results in at least about a 2-fold increase or more in transcription associated with a nucleic acid sequence, as compared to a control, e.g., in the absence of the saRNA molecule. In some embodiments, the increase in gene expression results in at least about a 2.5-fold increase or more, at least about a 3-fold increase or more, at least about a 3.5-fold increase or more, at least about a 4-fold increase or more, at least about a 4.5-fold increase or more, at least about a 5-fold increase or more, at least about a 5.5-fold increase or more, at least about a 6-fold increase or more, at least about a 6.5-fold increase or more, at least about a 7-fold increase or more, at least about a 7.5-fold increase or more at least about a 8-fold increase or more, and up to about 10-fold increase or more, including about 15-fold increase or more, about 20-fold increase or more, such as 25-fold increase or more. An increase in gene expression or activity can be measured by any of a variety of methods well known in the art. Suitable methods of examining gene expression or activity include measuring nucleic acid transcription level, mRNA level, enzymatic activity, methylation state, chromatin state or configuration, or other measure of nucleic acid activity or state in a cell or biological system.

After introduction of a saRNA molecule into a cell, the introduction results in a decrease in histone methylation (e.g., at a lysine). Accordingly, introduction of the saRNA molecule in the cell results in demethylation of a histone molecule, such as histone 3, usually at the lysine residue, e.g., a lysine 9 residue.

Because the ability of the modified dsRNAs of the present invention to retain functionality and resist degradation of the compound is not dependent on the sequence of the bases, the cell type, or the species into which it is introduced, the present invention is applicable across a broad range of mammals, including but not limited to humans. The present invention is particularly advantageous for use in mammals such as cattle, horse, goats, pigs, sheep, canines, rodents such as hamsters, mice, and rats, and primates such as, for example, gorillas, chimpanzees, and humans. Transgenic mammals may also be used, e.g. mammals that have a chimeric gene sequence. Methods of making transgenic animals are well known in the art, see, for example, U.S. Pat. No. 5,614,396.

The present invention may be used advantageously with diverse cell types including those of the germ cell line, as well as somatic cells. The cells may be stem cells or differentiated cells. For example, the cell types may be embryonic cells, oocytes sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

The present invention is applicable for use for activation (e.g., increasing expression) of a broad range of genes, including but not limited to the genes of a human genome, such as those implicated in diseases such as diabetes, Alzheimer's and cancer, as well as all genes in the genomes of the aforementioned organisms. Furthermore, the compositions and methods of the present invention may also be used to target a recombinant gene, such as a gene introduced on a nucleic acid vector.

The compositions and methods of the present invention may be administered to a cell or applied by any method that is now known or that comes to be known and that from reading this disclosure, one skilled in the art would conclude would be useful with the present invention. For example, the polynucleotides may be passively delivered to cells.

Passive uptake of modified polynucleotides can be modulated, for example, by the presence of a conjugate such as a polyethylene glycol moiety or a cholesterol moiety at the 5' terminal of the sense strand and/or, in appropriate circumstances, a pharmaceutically acceptable carrier.

The saRNA may be delivered to a cell by any method that is now known or that comes to be known and that from reading this disclosure, persons skilled in the art would determine would be useful in connection with the present invention in enabling saRNA to cross the cellular membrane and/or the nuclear membrane. These methods include, but are not limited to, any manner of transfection, such as for example transfection employing DEAE-Dextran, calcium phosphate, cationic lipids/liposomes, micelles, manipulation of pressure, microinjection, electroporation, immunoporation, use of vectors such as viruses (e.g., RNA virus), plasmids, cell fusions, and coupling of the polynucleotides to specific conjugates or ligands such as antibodies, antigens, or receptors, passive introduction, adding moieties to the saRNA that facilitate its uptake, and the like.

The stabilized dsRNAs of the present invention may be used in a diverse set of applications, including but not limited to basic research, drug discovery and development, diagnostics and therapeutics. For example, the present invention may be used to validate whether a gene product is a target for drug discovery or development. In this application, a target nucleic acid sequence of interest is identified for activation (e.g., increasing expression). For example, a cell is contacted with a saRNA specific for targeting the regulatory sequence of the particular target sequence of interest. The cell is maintained under conditions allowing for the methylation of the targeted DNA and/or methylation of nuclear proteins such as, for example, one or more histones, resulting in decreased activity or transcription of a gene. The extent of any increased activity, such as, for example, transcription or translation, of the gene is then assessed, along with the effect of such increased activity, and a determination is made that if activity is increased, then the nucleic acid sequence of interest is a target for drug discovery or development. In this manner, phenotypically desirable effects can be associated with saRNA activation of particular target nucleic acids of interest, and in appropriate cases toxicity and pharmacokinetic studies can be undertaken and therapeutic preparations developed.

The present invention may also be used in applications that induce transient or permanent states of disease or disorder in an organism by, for example, increasing the activity (e.g., by increasing transcription or translation) of a target nucleic acid of interest believed to be a cause or factor in the disease or disorder of interest in order to provide an animal model of a disease or disorder. Increased activity of the target nucleic acid of interest may render the disease or disorder worse, or tend to ameliorate or to cure the disease or disorder of interest, as the case may be. Likewise, increased activity of the target nucleic acid of interest may cause the disease or disorder, render it worse, or tend to ameliorate or cure it, as the case may be. Target nucleic acids of interest can comprise genomic or chromosomal nucleic acids or extrachromosomal nucleic acids, such as viral nucleic acids. Target nucleic acids of interest can include all manner of nucleic acids, such as, for example, non-coding DNA, regulatory DNA, repetitive DNA, reverse repeats, centromeric DNA, DNA in euchromatin regions, DNA in heterochromatin regions, promoter sequences, enhancer sequences, introns sequences, exon sequences, and the like.

Still further, the present invention may be used in applications, such as diagnostics, prophylactics, and therapeutics. For these applications, an organism suspected of having a disease or disorder that is amenable to modulation by manipulation of a particular target nucleic acid of interest is treated by administering saRNA. Results of the saRNA treatment may be ameliorative, palliative, prophylactic, and/or diagnostic of a particular disease or disorder. In representative embodiments, the saRNA is administered in a pharmaceutically acceptable manner with a pharmaceutically acceptable carrier with or without a diluent.

In some embodiments increasing expression of tumor suppressor genes is desirable. As such, agents that act to increase gene activity in such genes are useful in the treatment of a cellular proliferative disease, e.g., any condition, disorder or disease, or symptom of such condition, disorder, or disease that results from the uncontrolled proliferation of cells, e.g., cancer. Cancer is an example of a condition that is treatable using the compounds of the invention. Use of the saRNAs of the invention in combination with a second compound for use in treatment of a cellular proliferative disease is of particular interest. Exemplary cancers suitable for treatment with the subject methods include colorectal cancer, non-small cell lung cancer, small cell lung cancer, ovarian cancer, breast cancer, head and neck cancer, renal cell carcinoma, and the like.

Exemplary tumor suppressor genes include, but are not limited to, p53, p21, BRCA1, BRCA2, APC, RB1, CDKN2A, DCC, DPC4 (SMAD4), MADR2/JV18

(SMAD2), MEN1, MTS1, NF1, NF2, PTEN, VHL, WRN, and WT1. Other genes of interest include, but are not limited to, the nitric oxide synthase (NOS) genes, including NOS1 (nNOS) and NOS3 (eNOS), e-cadherin, growth factors, such as vascular endothelial growth factor (VEGF), neuronal growth factor (NGF), and the like.

Subjects suitable for treatment with a method of the present invention involving saRNAs include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but are not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neuroscular glaucoma and Oster Webber syndrome, psoriasis, restenosis, fungal, parasitic and viral infections such as cytomegaloviral infections. Subjects to be treated according to the methods of the invention include any individual having any of the above-mentioned disorders.

The invention should not be construed to be limited solely to the treatment of patients having a cellular proliferative disease. Rather, the invention should be construed to include the treatment of patients having conditions or disease associated with decreased expression of particular genes that would benefit from the methods of the subject invention.

Such subjects may be tested in order to assay the activity and efficacy of the subject saRNAs. Significant improvements in one or more of parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like).

Pharmaceutical Preparations Containing Compounds of the Invention

Also provided by the invention are pharmaceutical preparations of the subject saRNA compounds described above. The subject saRNA compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols, in a sterile vial or in a syringe. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc. The administration can be systemic or localized delivery of the formulation to a site in need of treatment, e.g., localized delivery to a tumor.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms of Compounds of the Invention

In pharmaceutical dosage forms, the subject saRNA compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject saRNA compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, intravenous routes, i.e., any route of administration other than through the alimentary canal, and local injection, with intra or peritumoral injection being of interest, especially where a tumor is a solid or semi-solid tumor (e.g., Hodgkins lymphoma, non-Hodgkins lymphoma, and the like). Local injection into a tissue defining a biological compartment (e.g., prostate, ovary, regions of the heart (e.g., pericardial space defined by the pericardial sac), intrathecal space, synovial space, and the like) is also of interest. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject saRNA compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol, collagen, cholesterol; and if desired, with conventional additives such as solubilizers, isotonic agents, suspending agents, emulsifying agents, stabilizers and preservatives.

The saRNA compounds can also be delivered to the subject by enteral administration. Enteral routes of administration include, but are not necessarily limited to, oral and rectal (e.g., using a suppository) delivery.

Furthermore, the subject saRNA compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Invention

Depending on the subject and condition being treated and on the administration route, the subject saRNA compounds may be administered in dosages of, for example, 0.1 μg to 100 mg/kg body weight per day. In certain embodiments, the therapeutic administration is repeated until a desired effect is achieved. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Dosages for a given compound are readily determinable by those of skill in the art by a variety of means.

Although the dosage used will vary depending on the clinical goals to be achieved, a suitable dosage range is one which provides up to about 1 μg to about 1,000 μg or about 10,000 μg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other agents that activate or suppress a biochemical activity, such as a chemotherapeutic agent. The subject compounds may be used to provide an increase in the effectiveness of another chemical, such as a pharmaceutical, or a decrease in the amount of another chemical, such as a pharmaceutical that is necessary to produce the desired biological effect.

Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

Furthermore, the saRNA compounds of the present invention may also be used in combination therapy with siRNA molecules. In such embodiments, the saRNA molecules may be administered to increase activation of a first gene and the siRNA molecule may be administered to silence expression of a second gene. For example, the saRNA molecules may be administered to increase activation of a tumor suppressor gene and the siRNA molecule may be administered to silence expression of an oncogene.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Representative compounds and unit doses are those described herein above.

In one embodiment, the kit comprises a saRNA formulation in a sterile vial or in a syringe, which formulation can be suitable for injection in a mammal, particularly a human.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials were used in the examples below.

saRNA Design and Synthesis

All saRNAs were manually designed and homology searches were done by querying the UCSC human genome database (available on the worldwide web at genome.ucsc.edu) to exclude sequences that share substantial homology with other untargeted sequences in the human genome database. Two control saRNAs (saControl and saCon-2) were specifically designed to lack homology to all known human sequences. saRNAs were chemically synthesized by Invitrogen (Carlsbad, Calif.) with dTdT 3' overhangs. At least two separate batches of synthesized saRNAs for each gene were used in transfection experiments. The saRNA sequences are described blow.

```
saEcad-P1 (-312/-284):
                                               (SEQ ID NO: 01)
Sense: 5'-AGAACUCAGCCAAGUGUAA[dT][dT]-3'
                                               (SEQ ID NO: 02)
Antisense: 5'-UUACACUUGGCUGAGUUCU[dT][dT]-3' saEcad-P1-26 (saEcad-P1 extended to 26 nucleotides
by adding 5 nucleotides to the 3' end):
                                               (SEQ ID NO: 03)
Sense: 5'-AGAACUCAGCCAAGUGUAAAAGCC[dT][dT]-3'
                                               (SEQ ID NO: 04)
Antisense: 5'-GGCUUUUACACUUGGCUGAGUUCU[dT][dT]-3' saEcad-P2 (-215/-197):
                                               (SEQ ID NO: 05)
Sense: 5'-AACCGUGCAGGUCCCAUAA[dT][dT]-3'
                                               (SEQ ID NO: 06)
Antisense: 5'-UUAUGGGACCUGCACGGUU[dT][dT]-3' saEcad-P2-5 (5-bp mutated at the antisense 5' end
of saEcad-P2):
                                               (SEQ ID NO: 07)
Sense: 5'-AACCGUGCAGGUCCUUAUC[dT][dT]-3'
                                               (SEQ ID NO: 08)
Antisense: 5'-GAUAAGGACCUGCACGGUU[dT][dT]-3' saEcad-P2-3 (5-bp mutated at the antisense 3'
end of saEcad-P2):
                                               (SEQ ID NO: 09)
Sense: 5'-CGUAAUGCAGGUCCCAUAA[dT][dT]-3'
                                               (SEQ ID NO: 10)
Antisense: 5'-UUAUGGGACCUGCAUUACG[dT][dT]-3' saEcad-P2-26 (saEcad-
P2 extended to 26 nucleotides by
adding 5 nucleotides to the 3' end):
                                               (SEQ ID NO: 11)
Sense: 5'-AACCGUGCAGGUCCCAUAACCCAC[dT][dT]-3'
                                               (SEQ ID NO: 12)
Antisense: 5'-GUGGGUUAUGGGACCUGCACGGUU[dT][dT]-3' saEcad-P2-16 (saEcad-P2 truncated to 16
nucleotides from its 5' end):
                                               (SEQ ID NO: 13)
Sense: 5'-UGCAGGUCCCAUAA[dT][dT]-3'
                                               (SEQ ID NO: 14)
Antisense: 5'-UUAUGGGACCUGCA[dT][dT]-3' saEcad-P3 (-56/-33):
                                               (SEQ ID NO: 15)
Sense: 5'-GCGGUACGGGGGGCGGUGCCUCCGG-3'
                                               (SEQ ID NO: 16)
Antisense: 5'-GGAGGCACCGCCCCCCGUACCGCUG-3' saEcad-837 (-166/-184):
                                               (SEQ ID NO: 17)
Sense: 5'-CUAGCAACUCCAGGCUAGA[dT][dT]-3'
                                               (SEQ ID NO: 18)
Antisense: 5'-UCUAGCCUGGAGUUGCUAG[dT][dT]-3' saEcad-947 (-56/-74):
                                               (SEQ ID NO: 19)
Sense: 5'-UGAACCCUCAGCCAAUCAG[dT][dT]-3'
                                               (SEQ ID NO: 20)
Antisense: 5'-CUGAUUGGCUGAGGGUUCA[dT][dT]-3' saEcad-962 (-41/-59):
                                               (SEQ ID NO: 21)
Sense: 5'-UCAGCGGUACGGGGGGCGG[dT][dT]-3'
                                               (SEQ ID NO: 22)
Antisense: 5'-CCGCCCCCCGUACCGCUGA[dT][dT]-3' saP21-322 (-322/-303):
                                               (SEQ ID NO: 23)
Sense: 5'-CCAACUCAUUCUCCAAGUA[dT][dT]-3'
                                               (SEQ ID NO: 24)
Antisense: 5'-UACUUGGAGAAUGAGUUGG[dT][dT]-3' saP21-322-G5' (5-bp mutated at the antisense 5'
end of saP21-322):
                                               (SEQ ID NO: 25)
Sense 5'-CCAACUCAUUCUCCCGUUC[dT][dT]-3'
                                               (SEQ ID NO: 26)
Antisense: 5'-GAACGGGAGAAUGAGUUGG[dT][dT]-3' saP21-322-G3' (5-bp mutated at the antisense 3'
end of saP21-322):
                                               (SEQ ID NO: 27)
Sense: 5'-UGUGGUCAUUCUCCAAGUA[dT][dT]-3'
                                               (SEQ ID NO: 28)
Antisense: 5'-UACUUGGAGAAUGACCACA[dT][dT]-3' saP21-322-m (5-bp mutated in the middle region
of saP21-322):
                                               (SEQ ID NO: 29)
Sense: 5'-CCAACUUUCCAUCCAAGUA[dT][dT]-3'
                                               (SEQ ID NO: 30)
Antisense: 5'-UACUUGGAUGGAAAGUUGG[dT][dT]-3' saVEGF-706 (-706/-688):
                                               (SEQ ID NO: 31)
Sense: 5'-GCAACUCCAGUCCCAAAUA[dT][dT]-3'
                                               (SEQ ID NO: 32)
Antisense: 5'-UAUUUGGGACUGGAGUUGC[dT][dT]-3' saControl:
                                               (SEQ ID NO: 33)
Sense: 5'-ACUUACGAGUGACAGUAGA[dT][dT]-3'
                                               (SEQ ID NO: 34)
Antisense: 5'-UCUACUGUCACUCGUAAGU[dT][dT]-3' saCon-2
                                               (SEQ ID NO: 35)
Sense: 5'-ACUACUGAGUGACAGUAGA[dT][dT]-3'
                                               (SEQ ID NO: 36)
Antisense: 5'-UCUACUGUCACUCAGUAGU[dT][dT]-3'
``` siRNA Design and Synthesis

The Ago specific siRNAs were synthesized as described in Meister et al., Mol. Cell. 15:185 (2004). The siRNA sequences are described blow.

```
siAgo2
                                               (SEQ ID NO: 37)
Sense: 5'-GCACGGAAGUCCAUCUGAAUU-3'
```

-continued

```
                                          (SEQ ID NO: 38)
Antisense: 5'-pUUCAGAUGGACUUCCGUGCUU-3' siAgo1
                                          (SEQ ID NO: 39)
Sense: 5'-GAGAAGAGGUGCUCAAGAAUU-3'
                                          (SEQ ID NO: 40)
Antisense: 5'-pUUCUUGAGCACCUUCUCUU-3' siAgo3
                                          (SEQ ID NO: 41)
Sense: 5'-GAAAUUAGCAGAUUGGUAAUU-3'
                                          (SEQ ID NO: 42)
Antisense: 5'-pUUACCAAUCUGCUAAUUUCUU-3' siAgo4
                                          (SEQ ID NO: 43)
Sense: 5'-GGCCAGAACUAAUAGCAAUUU-3'
                                          (SEQ ID NO: 44)
Antisense: 5'-pAUUGCUAUUAGUUCUGGCCUU-3' siAgoC
                                          (SEQ ID NO: 45)
Senske: 5'-UUCUCCGAACGUGUCACGUUU-3'
                                          (SEQ ID NO: 46)
Antisense: 5'-pACGUGACACGUUCGGAGAAUU-3'
```

Cell Culture and Transfection

Human prostate cancer cell lines PC-3, DU-145, and LNCaP were maintained in RPMI-1640 medium supplemented with 10% fetal bovine serum (FBS), 2 mM L-glutamine, penicillin (100 U/ml), and streptomycin (100 µg/ml) in a humidified atmosphere of 5% $CO_2$ maintained at 37° C. HeLa, J82, T24, HEK293 cells were maintained in minimum essential medium (Eagle) supplemented with 2 mM L-glutamine, Earle's BSS, penicillin, streptomycin, and 10% FBS. MCF-7 and HeLa cells were supplemented with an additional 1 mM sodium pyruvate and 0.01 mg/ml bovine insulin. The day before transfection cells were plated in growth medium without antibiotics at a density of 50-60%. Transfections of saRNA were carried out using Lipofectamine 2000 (Invitrogen) according to the manufacture's protocol and lasted for 72 hrs (exceptions occurred during time course experiments). HeLa cells were transfected with E-cadherin saRNAs in the presence of 1-10 µM 5-azacytidine. Interferon-α2a (Sigma, St. Louis, Mo.) treatment was performed on PC-3 cells at the specified concentrations.

Nucleic Acid Extraction

Total cellular RNA and genomic DNA were extracted using TriReagent™ (Molecular Research Center, Inc., Cincinnati, Ohio) by following the manufacturer's instructions.

Western Analysis

Cultured cells were washed with PBS and lysed with M-PER protein extraction buffer (Pierce Biotechnology, Inc., Rockford, Ill.). The cell lysates were centrifuged at 12,000 g for 10 minutes, and the supernatant was collected. The proteins were quantified and then diluted to the same concentration. The samples were separated using 7.5-15% sodium dodecyl sulfate-polyacrylamide gels. The separated proteins were transferred to polyvinylidene difluoride membranes and the membranes were blocked overnight with 5% non-fat dry milk. The membranes were immunoblotted with anti-β-actin (Sigma, Saint Louis, Mich.), anti-GAPDH (Chemicon, Temecula, Calif.), anti-E-cadherin (Zymed, S. San Francisco, Calif.), or anti-P21 (Upstate Biotechnology, Lake Placid, N.Y.) antibodies for one hour, then washed for five minutes. The membranes were then incubated with anti-E-cadherin (Zymed, South San Francisco, Calif.) or anti-p21 (Upstate) for another hour. After three five-minute washes, the membranes were incubated with secondary antibody. Immunoreactive proteins were detected by SuperSignal West Dura Lumino/Enhancer Solution (Pierce).

Immunocytochemistry

Immunostaining for E-cadherin was performed on monolayer cells grown on glass cover slips (Nalge Nunc International, NY). Cells were fixed 72 hours after transfection in 4% paraformaldehyde (20 min) and subjected to sequential 70%, 90%, and 100% ethanol baths. After immersing the slips in blocking buffer for 30 min, mouse anti-E-cadherin (Zymed) was added and incubated at 4° C. overnight. Immunostaining was visualized with fluorescein isothiocyanate (FITC)-labeled secondary antibody (Zymed). Nuclear counterstaining with propidium iodide (Molecular Probes, OR) was performed after the removal of excess secondary antibody. The slides were photographed with a Leica confocal laser microscope (Leica Microsystems Inc., PA) under 800× magnification. Control experiments were carried out omitting the primary antibody.

Bisulfite Modification of Genomic DNA, PCR Amplification and Cloning

Primers for bisulfite genomic sequencing PCR were designed using the online program, MethPrimer previously developed (Li et al., Bioinformatics 18:1892-1897 (2004)). Bisulfite modification of DNA (1 µg) was performed using the CpGenome DNA Modification Kit (Chemicon) according to the manufacturer's instructions. The bisulfite-modified DNA were amplified as previously described (Li et al., Cancer Res. 60:702-706 (2000)). PCR products were cloned into the pCR2.1 plasmid (Invitrogen) and transformed into TOP10 cells (Invitrogen). Ten positive clones from each PCR reaction were picked at random and grown overnight in 2 ml LB medium. Plasmid DNA was isolated and sequenced. Primers for bisulfite sequencing PCR are described below.

```
E-cadherin
                                          (SEQ ID NO: 47)
S1 (sense): 5'-ATTTTAGTTTGGGTGAAAGAGTGAG-3'
                                          (SEQ ID NO: 48)
S2 (antisense): 5'-AACCCTCTAACCTAAAATTACTAAAAT
CTA-3'
Product of S1 and S2: -370 to -161

(SEQ ID NO: 49)
S3 (sense): 5'-TTTAGTAATTTTAGGTTAGAGGGTTAT-3'
                                          (SEQ ID NO: 50)
S4 (antisense): 5'-AAACTCACAAATACTTTACAATTCC-3'
Product of S3 and S4: -193 to +35.
```

Chromatin Immunoprecipitation (ChIP) Assay

The ChIP assays were performed using a ChIP assay kit (Upstate Biotechnology, Lake Placid, N.Y.) by following the vendor's instructions. Briefly, cells were saRNA transfected in 100 mm dishes for 72 hours. Formaldehyde was then added to the cells to a final concentration of 1% and incubated at 37° C. for 10 minutes. The cells were then lysed and sonicated. The sonicated samples were pre-cleaned with a salmon sperm DNA/protein A agarose slurry and incubated overnight at 4° C. with or without antibodies. The antibody which recognizes histone demethylation at lysine 9 (H3m2K9) and lysine 4 (H3m2K4) (Upstate) were used to detect specific changes in histone methylation patterns. Chromatin-antibody complexes were collected using a salmon sperm DNA/protein A agarose slurry and reverse crosslinked after washes. Immunoprecipitated DNA was analyzed by PCR. PCRs were performed for 25 to 32 cycles of 95° C. for 30 seconds, 60° C. for 30 seconds, and 72° C. for 30 seconds. ChIP PCR primers that were used are as follows:

```
E-cadherin ChIP Primers (-359/-71)
                                        (SEQ ID NO: 51)
Sense: 5'-GGTGAAAGAGTGAGCCCCATCTC-3';
                                        (SEQ ID NO: 52)
Antisense: 5'-TTCACCTGCCGGCCACAGCCAATCA-3'.

p21 Promoter Primers (-434/-278)
                                        (SEQ ID NO: 53)
Sense: 5'-CAGCTGCATTGGGTAAATCC-3'
                                        (SEQ ID NO: 54)
Antisense: 5'-GACACATTTCCCCACGAAGT-3'
```

Semi-Quantitative RT-PCR

Semi-quantitative RT-PCR was performed using the Titanium One-Step RT-PCR kit (BD Biosciences, Palo Alto, Calif.) throughout the E-cadherin saRNA transfection experiments. Total cellular RNA (50 ng) was used for each reverse-transcription reaction. For p21 and VEGF saRNA transfection experiments, 1 μg of total RNA was reverse transcribed using SuperScript™ reverse transcriptase (Invitrogen) and oligo(dT) primers. The resulting cDNA samples were amplified by PCR using primers specific for E-cadherin, p21, VEGF, Ago2, GAPDH, OAST, or OAS3. Amplification of GAPDH served as a loading control. cDNA samples were also generated using random hexamer primers for amplification of potential cryptic transcripts located in the p21 and E-cadherin promoters. RT-PCR primer sequences were as follows:

```
E-cadherin:
                                        (SEQ ID NO: 55)
Sense: 5'-CCTGGGACTCCACCTACAGA-3'
                                        (SEQ ID NO: 56)
Antisense: 5'-GGATGACACAGCGTGAGAGA-3'

GAPDH:
                                        (SEQ ID NO: 57)
Sense: 5'-TCCCATCACCATCTTCCA-3'
                                        (SEQ ID NO: 58)
Antisense: 5'-CATCACGCCACAGTTTCC-3'

β-actin:
                                        (SEQ ID NO: 59)
Sense: 5'-TCTACAATGAGCTGCGTGTG-3'
                                        (SEQ ID NO: 60)
Antisense: 5'-ATCTCCTTCTGCATCCTGTC-3'

OAS1:
                                        (SEQ ID NO: 61)
Sense: 5'-GCTGGAAGCCTGTCAAAGAG-3'
                                        (SEQ ID NO: 62)
Antisense: 5'-GAGCTCCAGGGCATACTGAG-3'

OAS3:
                                        (SEQ ID NO: 63)
Sense: 5'-TACCACCAGGTGTGCCTACA-3'
                                        (SEQ ID NO: 64)
Antisense: 5'-AAAGCATGGGTGGTCATAGC-3' p21
                                        (SEQ ID NO: 65)
Sense: 5'-GCCCAGTGGACAGCGAGCAG-3'
                                        (SEQ ID NO: 66)
Antisense: 5'-GCCGGCGTTTGGAGTGGTAGA-3' p53
                                        (SEQ ID NO: 67)
Sense: 5'-CCTCACCATCATCACACTGG-3'
                                        (SEQ ID NO: 68)
Antisense: 5'-TCTGAGTCAGGCCCTTCTGT-3'

VEGF
                                        (SEQ ID NO: 69)
Senese: 5'-CCCACTGAGGAGTCCAACAT-3'
                                        (SEQ ID NO: 70)
Antisense: 5'-AAATGCTTTCTCCGCTCTGA-3'

Ago1:
                                        (SEQ ID NO: 71)
Sense: 5'-GCGAATTGGGAAGAGTGGTA-3'
                                        (SEQ ID NO: 72)
Antisense: 5'-GCAGGTGCTGGGATAGAGAC-3'

Ago2:
                                        (SEQ ID NO: 73)
Sense: 5'-CGCGTCCGAAGGCTGCTCTA-3'
                                        (SEQ ID NO: 74)
Antisense: 5'-TGGCTGTGCCTTGTAAAACGCT-3'

Ago3:
                                        (SEQ ID NO: 75)
Sense: 5'-ATCCCAGCTGGAACAACAGT-3'
                                        (SEQ ID NO: 76)
Antisense: 5'-GCGTACGTAAGTGTGGCAGA-3'

Ago4:
                                        (SEQ ID NO: 77)
Sense: 5'-GGGTAGGGAAAAGTGGCAAT-3'
                                        (SEQ ID NO: 78)
Antisense: 5'-GAGCGAGTGCACCTCACATA-3'
```

Establishment of Mice Xenograft Tumor Model

Twelve athymic nude, homozygous male mice at the age of 4 weeks were purchased from Simonsen Laboratories, Inc. After 5 days of acclimatization period, a total of $5.0 \times 10^6$ PC-3 cells were inoculated subcutaneously (s.c.) in 0.3 ml of PBS through a 25-gauge needle into the lower flank of the mice. After 2 weeks when tumors reached an average volume of ~55 $mm^3$, the tumor-bearing nude mice were randomly divided into two treatment groups with one group treated with a p21 saRNA (saP21-322) and the other with a control saRNA (saControl).

saRNA Delivery to Animal saRNA intratumoral delivery was performed using in vivo jetPEI™ (PolyPlus Transfection, Illkirch, France), a linear polyethylenimine (PEI). Forty microgram saRNA (Invitrogen) dissolved in 5% glucose was mixed with 6.4 μl in vivo jetPEI™ also dissolved in 5% glucose (N/P ratio: 8). The mixture was allowed to stand at room temperature for 15 min before injection. The resulting PEI-saRNA complex was injected into tumor using a gauge-27 needle. The saRNA injection was repeated every 3 days for nine days for a total of 3 injections. Mice body weight and tumor size were recorded every week. After four weeks following the initial treatment, mice were sacrificed and tumors were removed and weighted. Tumor volume in $mm^3$ was calculated by the formula: volume=(width)$^2$×length/2.

Immunohistochemistry

Paraffin-embedded tumor blocks were cut at 5 μm and the sections were dried at 55° C. for 1 hour. After rehydration with buffer (0.05 M PBS, pH 7.4), sections were treated with 0.3% hydrogen peroxidase in methanol for 10 min. to inactivate endogenous peroxidase. Antigen retrieval was done by autoclaving the slides for 10 minutes in 10 mM citrate, pH 6.0. After blocking with 3% normal goat serum for 4 hr, sections were incubated with primary antibody anti-p21 (Chemicon), at 1:100 dilution in PBS, overnight at 4° C. under a humid chamber. Sections were washed with 20 mM Tris, 150 mM NaCl, 0.025% Tween, pH 7.8, and then incubated with the secondary antibody for 30 min. Immunostaining was done by the avidin-biotin-peroxidase method (Elite ABC, Vector Lab, Burlingame, Calif.), using diaminobenzidine as the chromogen, followed by counterstaining with hematoxylin.

Example 1 saRNA Targeting the E-Cadherin Gene Promoter Induce E-Cadherin mRNA and Protein Expression To test whether the epigenetic code could be targeted to induce protein expression, two 21-nucleotide small activating RNAs (saRNAs) directed against the E-cadherin promoter were designed and chemically synthesized. One of the saRNAs (saEcad-P1) was designed to target a region upstream of the CpG island on the E-cadherin promoter (−312/−284, relative to the transcription start site); the second saRNA (saEcad-P2) was designed to target the 5' boundary of the CpG island (−215/−197). A 21-nucleotide control saRNA (saControl) lacking homology to known human sequences was also designed. PC-3 cells, which are human prostate cancer cell line that has low constitutive expression of E-cadherin, were chosen for analysis.

Dramatic induction of E-cadherin protein expression in PC-3 cells transfected with saEcad-P1 or saEcad-P2 was observed within 72 hours of transfection compared to mock transfected cells (FIG. 1, panel A, and FIG. 2). saEcad-P1 and saEcad-P2 caused a 3.1 and 8.4-fold increase in protein expression, respectively. When the two saRNAs were used in combination, E-cadherin expression was further enhanced (13.4 fold induction). E-cadherin mRNA expression was also induced by both saEcad-P1 and saEcad-P2 with the magnitude of change very similar to that of protein expression (FIG. 1, panel B), indicating that the induction was at the transcriptional level. saControl however, showed no effect on E-cadherin mRNA and protein expression (FIG. 1, panels A and B, and FIG. 2), showing that the induction of E-cadherin by saRNAs is sequence-specific. These results were reproducible in at least five independent experiments using saRNA synthesized from two separate batches, saRNA induced E-cadherin expression was further confirmed by immunocytochemistry which revealed that in cells transfected with saEcad-P2, E-cadherin staining was much more intense than that in mock and saControl transfected cells (FIG. 3).

Figure 2:
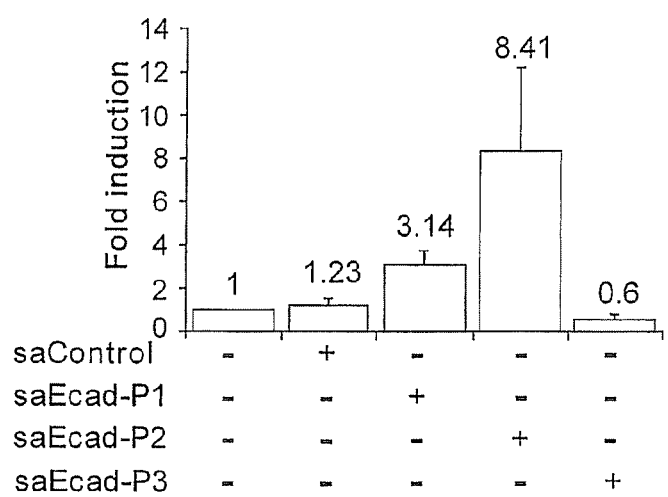
FIG. 2 is a graph showing fold changes in E-cadherin protein expression in PC-3 cells treated as in FIG. 1. Expression was normalized to that of β-actin. The results are presented as the mean±SEM of five independent experiments (at least two sample repeats within each experiment) except for saEcad-P3 transfection which was repeated twice.
Figure 3:
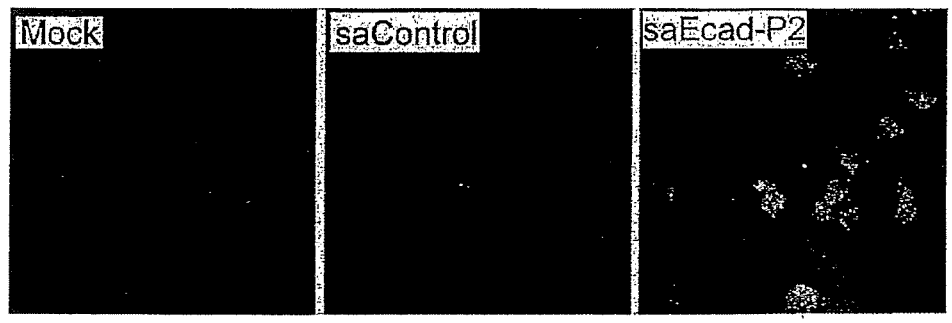
FIG. 3 is an image of immunofluorescence staining for E-cadherin in mock, saControl and saEcad-P2 transfected PC-3 cells. Transfection was carried out using 50 nM saRNA for 72 hours. Note the higher level of green fluorescence intensity from the saEcad-P2 transfected cells makes the cells appear larger than mock or saControl transfected cells although all images were taken under the same magnification (800×).

A third saRNA (saEcad-P3), which is 25-nucleotides in length and has a high GC content (84%), did not induce E-cadherin expression (FIG. 1, panels A and B, lanes 9 and 10, and FIG. 2).

Figure 4:
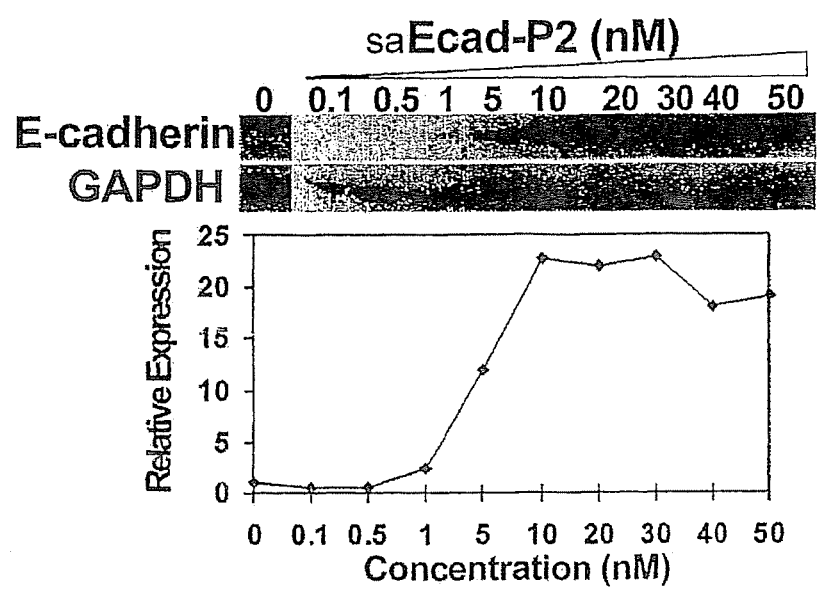
FIG. 4 is a Western blot (top panel) showing that saRNA transfection causes dose-dependent induction of E-cadherin protein expression. PC-3 cells were treated with saEcad-P2 at the indicated concentration for 72 hours. The bottom panel is a graph showing relative expression of E-cadherin at the indicated concentrations of saRNA.
Figure 5:
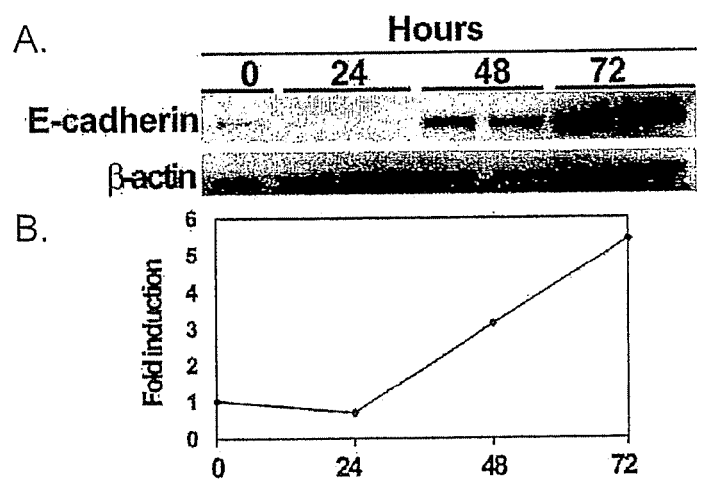
FIG. 5, panel A is a Western blot showing Expression of E-cadherin in PC-3 cells treated with 50 nM saEcad-P2 for the indicated periods of time. Panel B is a graph showing the fold induction of expression of E-cadherin of panel A.

Example 2 saRNAs Targeting the E-Cadherin Promoter Induce Prolonged E-Cadherin Expression and Cell Death H To further characterize saRNA-directed transcriptional activation (RdTA) additional studies were performed using saEcad-P2. A dose-response experiment showed that saEcad-P2 induced E-cadherin expression at concentrations as low as 1 nM and the induction was dose-dependent at concentrations ranging from 1 to 10 nM (FIG. 4). Doses higher than 10 nM caused no further increase in E-cadherin expression. A time course experiment showed that induction of E-cadherin protein expression occurred within 48 hours of saRNA transfection and peaked at 72 hours (FIG. 5, panels A and B).

Figure 6:
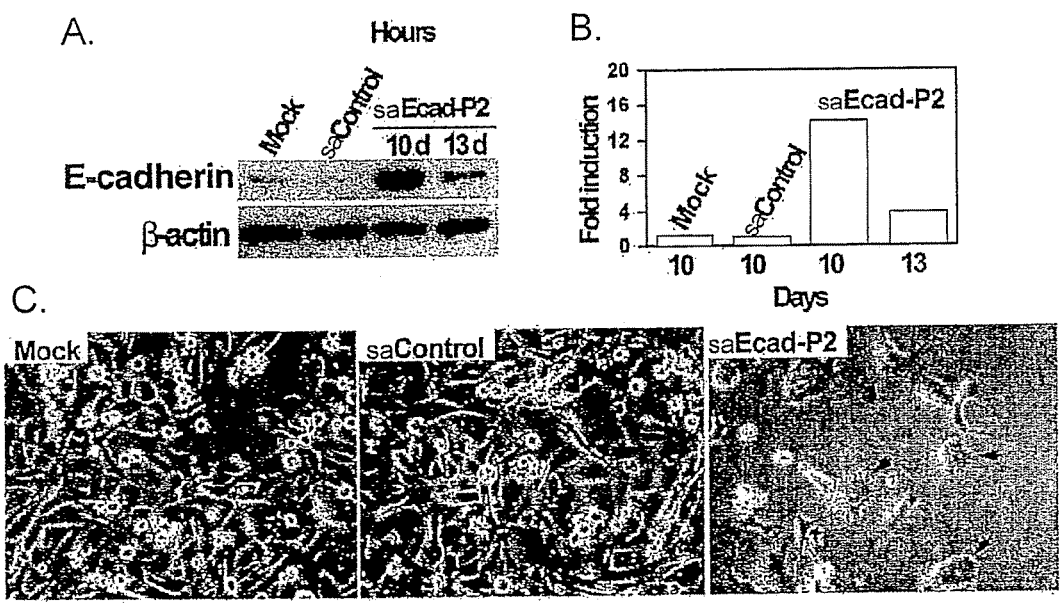
FIG. 6, panel A is Western blot showing expression of E-cadherin in PC-3 cells that were mock transfected or transfected with 50 nM of saControl or saEcad-P2 for the periods of time as indicated. Panel B is a graph showing the fold induction of E-cadherin expression in the cells of panel A. Panel C is a series of images showing PC-3 cells that were mock, saControl or saEcad-P2 transfected. Representative images were taken under phase-contrast microscopy (200×) on day 8 following transfection. Membrane protrusions like filopodia are indicated by arrows.

Longer periods of transfection in PC-3 cells were also tested. Mock and saControl transfected cells maintained healthy growth after transfection, while saEcad-P2 transfected cells gradually lost viability from day 5 (FIG. 6, panel C). No cells survived after 14 days. This finding is consistent with previous studies in which forced expression of E-cadherin results in inhibition of cell growth by mediating cell cycle arrest and apoptosis (Hsu et al., Am J Pathol 156:1515-25 (2000); Stockinger et al., J Cell Biol 154:1185-96 (2001)). In addition, filopodia formation, finger-like projections in siEcad-P2 transfected cells (FIG. 6, panel C) were also observed. This phenotype is associated with increased adhesion and can be induced by E-cadherin (Kim et al., J Biol Chem 275:36999-7005 (2000)).

To examine the lasting effect of saRNA activation, E-cadherin protein expression in cells that had been transfected for 10 and 13 days was also determined. An evaluation longer than 13 days was impossible due to cell death. Unexpectedly, a 14 and 3.8-fold increase was detected in E-cadherin expression in siEcad-P2 transfected cells on day 10 and day 13 respectively compared to that in 10 day mock transfected cells (FIG. 6, panels A and B), indicating that RdTA is sustainable and could be permanent. This observation is intriguing because classic RNAi by siRNA transfection is thought to be transient and the effect is usually lost by 5-7 days when the siRNA is exhausted (Dykxhoorn et al., Nat Rev Mol Cell Biol 4:457-67 (2003); Novina et al., Nat Med 8:681-6 (2002); and Tuschl et al., Nat Biotechnol 20:446-8 (2002)). A plausible explanation for the long-lasting transcriptional induction is that saRNA, after binding to its DNA target, imprints an epigenetic mark involving changes in histone modifications that is maintained across cell divisions in the absence of the saRNA. Thus, whether epigenetic mechanisms were involved in RdTA was later tested.

Example 3 saRNAs Induce E-Cadherin Expression in DU145 and HeLa Cells

Figure 7:
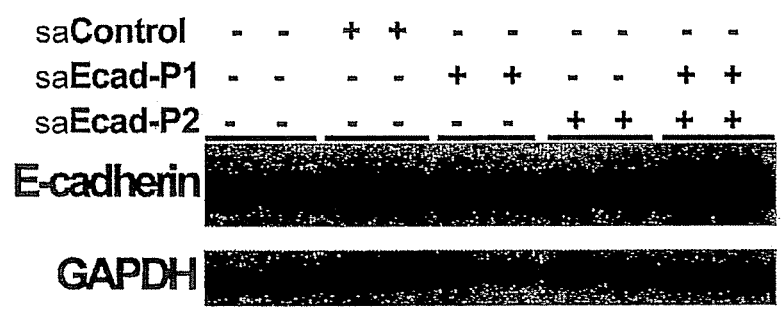
FIG. 7 shows that saRNAs induce E-cadherin expression in DU145 cells. Panel A is a Western blot showing protein expression of E-cadherin and GAPDH in DU145 cells that were transfected with 50 nM siRNA for 72 hours. Panel B is a graph showing fold induction of E-cadherin protein expression in cells as in panel A, normalized to that of GAPDH. The data are presented as the mean±SEM of four independent experiments (at least two sample repeats within each experiment) except for the combinational transfection using saEcad-P1 and saEcad-P2 which was repeated twice.
Figure 7:
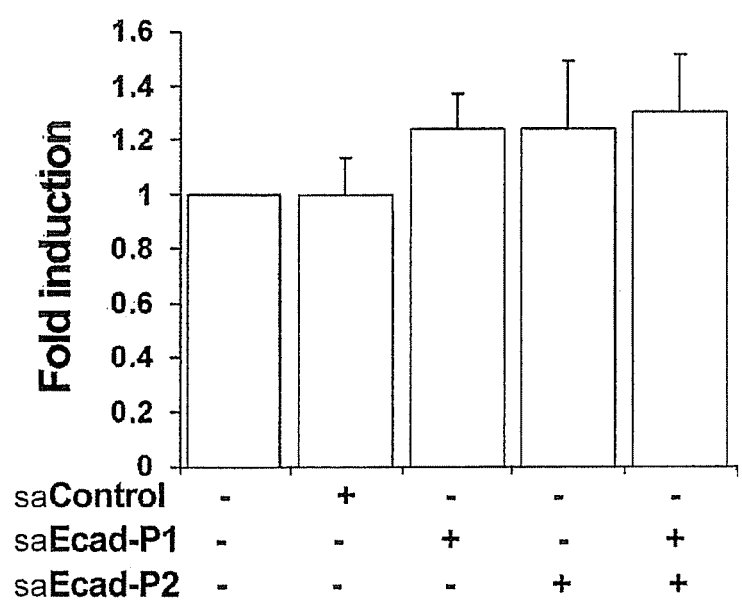
Figure 8:
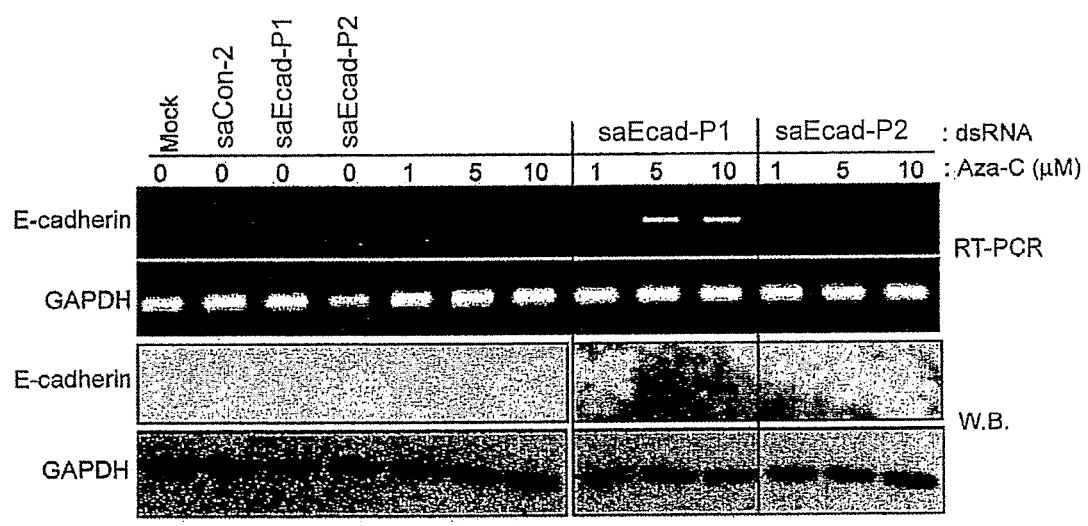
FIG. 8 shows that Aza-C enhances saRNA-induced expression of E-cadherin in HeLa cells. HeLa cells were transfected with 50 nM saRNA in the presence or absence of 1-10 μM Aza-C for 72 hrs. E-cadherin mRNA and protein levels were evaluated by RT-PCR and Western blot (W.B.) analysis, respectively. GAPDH levels were also determined and served as loading controls. E-cadherin protein was only detectable in cells co-treated with saEcad-P1 and Aza-C.

To test whether RdTA occurs in other cells, the saRNAs were transfected into a human prostate cancer cell line DU145 and a cervical cancer cell line HeLa cells. In DU145, the E-cadherin CpG island is not methylated (FIG. 19, panel C) and the cells express normal levels of E-cadherin (FIG. 7, panel A and B). A moderate and consistent level of induction of E-cadherin protein and mRNA expression was observed in DU145 cells in response to saEcad-P1 and saEcad-P2 treatment (FIG. 7, panels A and B). In contrast, HeLa cells do not express E-cadherin and the E-cadherin CpG island is heavily methylated. saRNA transfection (72 hours) failed to induce E-cadherin expression as detected by Western blotting. It is likely that pre-established methylation of the CpG island may prevent saRNA from activating transcription. To test this hypothesis, HeLa cells were transfected in the presence of low concentrations (1-10 µM) of 5'-aza-cytidine (Aza-C). Aza-C alone induced low-levels of E-cadherin mRNA expression (FIG. 8 RT-PCR). However, when cells were treated with both low-dose Aza-C and saRNA, E-cadherin expression elevated to levels much greater than treatment of Aza-C alone (FIG. 8). E-cadherin protein was only detectable by Western blot analysis in cells co-treated with Aza-C and saEcad-P1 (FIG. 8, W.B.). These findings support the view that suppressive methylation marker on gene promoter may prevent saRNA from activating transcription.

Example 4 saRNA Induces E-Cadherin Expression and Inhibition of Tumor Growth/Metastasis In Vivo An orthotopic prostate cancer/metastasis model is established by inoculating $2 \times 10^6$ PC-3 prostate cancer cells into the dorsolateral lobe of the prostate gland of eight week-old immune-deficient BALB/c nude mice (nu/nu) under total body anesthesia. Mice are given saRNA using hydrodynamic transfection method at week 2, 3 and 4. Briefly, 50 μg saEcad-P2 and saControl is dissolved in 1 ml PBS and the resulting solution is rapidly injected into the tail vein. For mock treatment, 1 ml PBS is injected.

The mice are sacrificed on week 8 after tumor cell inoculation. Primary tumors in the prostate are excised en bloc and weighed. All external iliac and sacral lymph nodes as well as other macroscopically enlarged regional lymph nodes are harvested in all mice. The lungs are collected with the mediastinal lymph nodes and heart. The liver, brain and long bones in 4 limbs are also isolated from each mouse. These tissues are fixed in 10% formalin and embedded in paraffin and are cut at 15 μm intervals for hematoxylin and eosin staining. Tumor and metastatic disease are confirmed by histological examination. E-cadherin expression in the prostate is evaluated by immunohistochemistry.

Example 5 saRNA Induces p21 mRNA and Protein Expression p21 Waf1/Cip1/Sdi1 (p21) was the first identified inhibitor of the cyclin/cyclin-dependent kinase (CDK) complex and is one of the principal checkpoint control proteins which negatively regulate cell proliferation. p21 was chosen for saRNA induced expression as another example that small double-stranded RNAs can activate gene transcription. A 21-nucleotide saRNA (saP21-322) was designed targeting the p21 gene promoter sequence at position −322 relative to the transcriptional start site of p21 and chemically synthesized.

Figure 9:
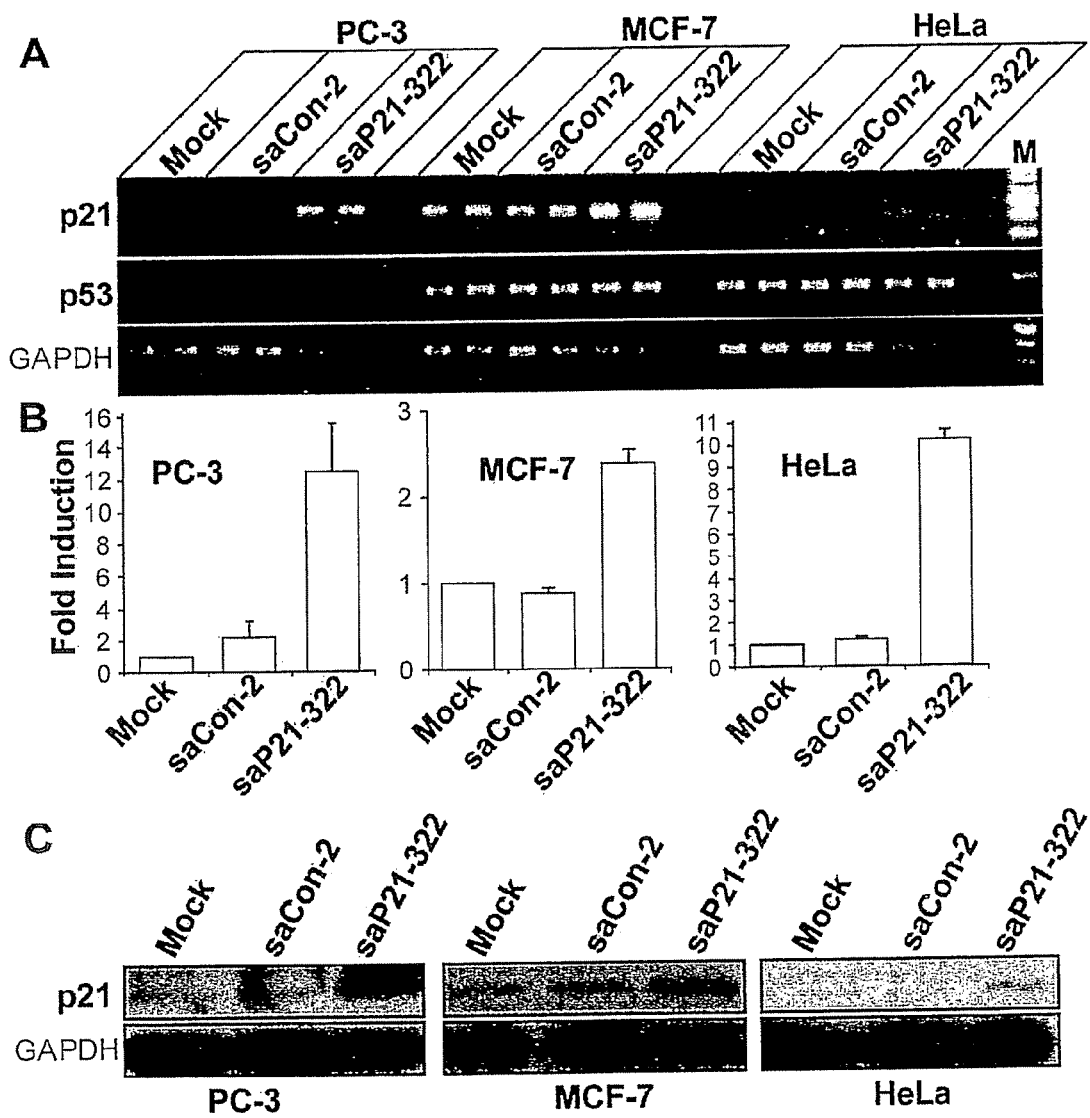
FIG. 9 shows saRNA induction of p53-independent p21 mRNA and protein expression in PC-3, MCF-7 and HeLa cells. Cells were transfected with 50 μM saRNAs for 72 hrs. Panel A is a gel showing mRNA levels in cells treated with saRNA for p21 (saP21-322), negative control (mock and saCon-2) in PC-3 cells, MCF-7 cells, and HeLa cells (M-molecular weight marker). Panel B shows mRNA expression of p21 normalized to that of GAPDH. The results are presented as the mean±SEM of two independent experiments with duplicate samples within each experiment. Cells treated with saP21-322 saRNA resulted in a 12.5, 2.4 and 10.1-fold increase in p21 expression in PC-3, MCF-7 and HeLa cells respectively. Panel C is a Western blot showing p21 and GAPDH protein expression using anti-p21 and anti-GAPDH antibody. The level of p21 protein induction by saP21-322 saRNA was consistent with that of mRNA induction as detected by RT-PCR.
Figure 10:
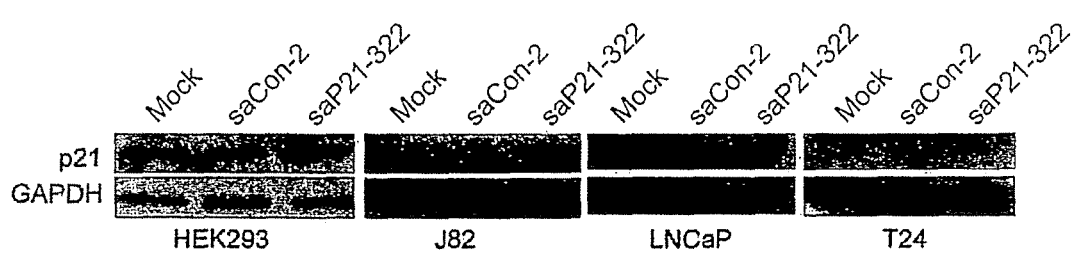
FIG. 10 is a Western blot showing p21 saRNA induced p21 protein expression in HEK-293, J82, LNCaP, and T24 cells. Cells were transfected with 50 μM saRNAs for 72 hrs.

To test whether the saRNA molecule saP21-322 induces p21 expression, saP21-322 was transfected into human PC-3, MCF-7 and HeLa cells. As shown in FIG. 9, saP21-322 caused significant increase in p21 mRNA and protein expression in all cells tested. In addition, p53 expression was not affected by saRNA transfection. Four additional cell lines were also tested, including human embryonic kidney cell HEK-293, bladder cancer cells J82 and T24, and human prostate cancer cell line LNCaP. The results show (FIG. 10) that transfection of the saRNA molecule saP21-322 caused different degree of p21 protein induction.

As shown above, a single saRNA targeting the human p21 promoter induce robust p21 expression at both mRNA and protein level in all cell lines tested. This induction is sequence-specific because a control saRNA lacking homology to any sequence does not induce p21 expression. In addition, p21 induction by the saRNA is p53-independent because no expression changes for p53 were observed in any saRNA transfected cells and PC-3 cells are p53 null.

Figure 11:
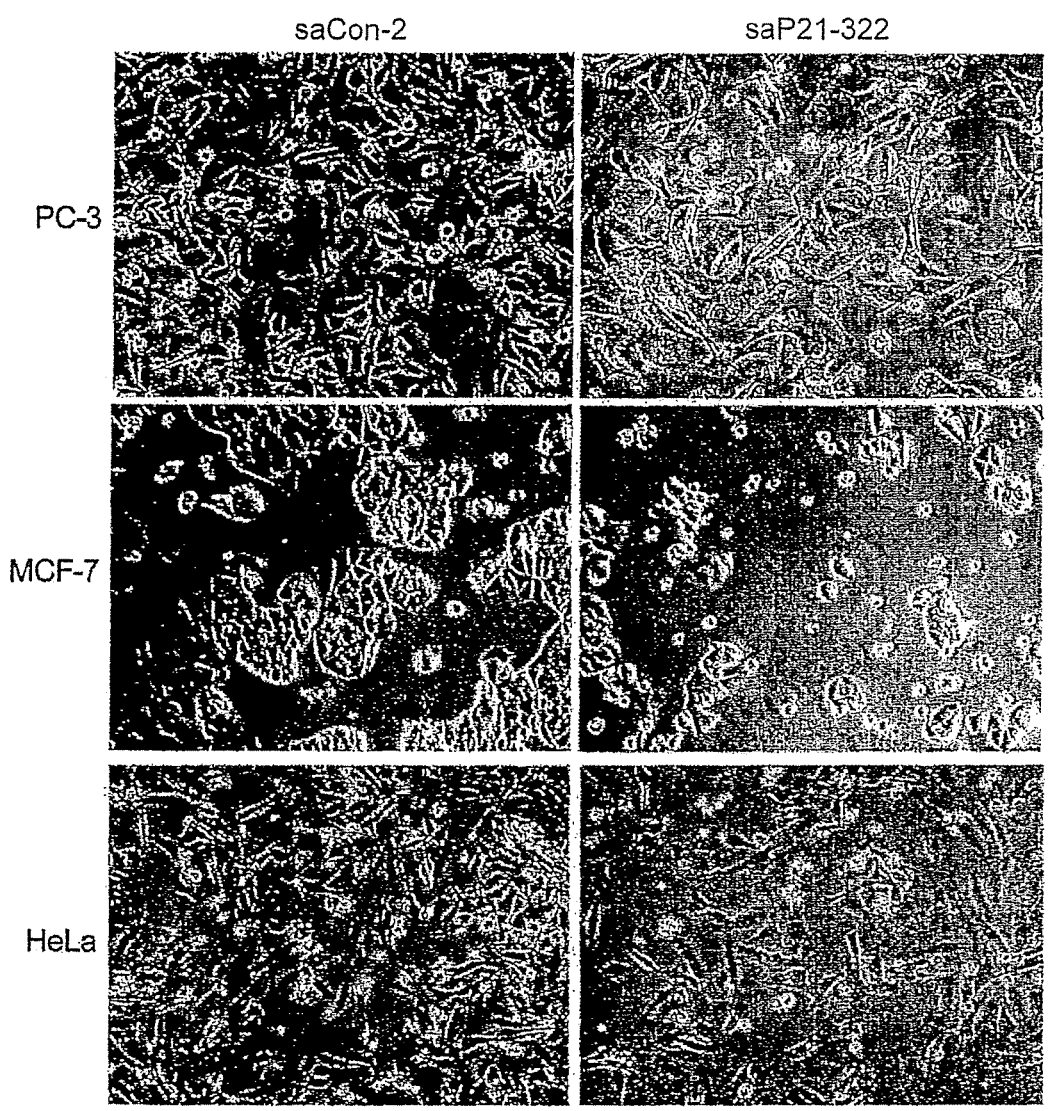
FIG. 11 shows images of tumor cells treated with the saRNA molecule saP21-322. PC-3, MCF-7 and HeLa cells were transfected with either control saRNA saCon-2 or saP21-322. Cell images were taken 72 hrs after transfection under 100× magnification. saP21-322 transfection caused inhibition of cell proliferation in PC-3, MCF-7 and HeLa.

Example 6 saRNA Inhibits Tumor Cell Proliferation In Vitro p21 is a known cell cycle negative regulator. Therefore it was postulated that an increase in expression of p21 in cultured cells would result in inhibition of cell proliferation. PC-3, MCF-7, and HeLa cells were transfected with either the control saCon-2 or the p21 saRNA molecule saP21-322. The results show that saP21-322 saRNA transfected cells experiences a significantly slowed growth compared to cells transfected with the control saRNA molecule saCon-2 (FIG. 11).

Example 7 saRNA Induces VEGF Expression

Figure 12:
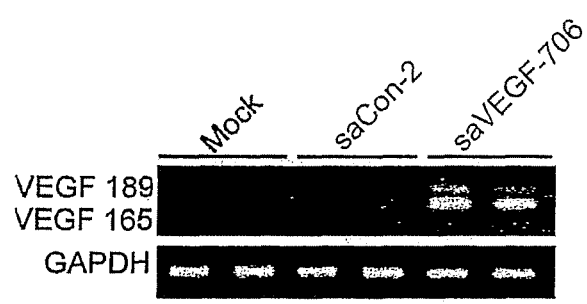
FIG. 12 shows saRNA induced VEGF expression in HeLa cells. HeLa cells were plated in 6-well plate and transfected with mock, saCon-2 or saVEGF-706 for 72 hrs. mRNA expression was evaluated by RT-PCR. Panel A is a gel showing RT-PCR amplified mRNA of two isoforms (VEGF 189 and 165) of VEGF. Panel B shows VEGF mRNA expression normalized to that of GAPDH. A 3.7 and 4-fold increase in VEGF-189 and -165 respectively was observed compared to mock transfected cells.
Figure 12:
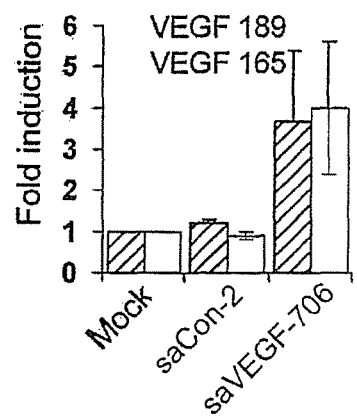

To further test the generality of RdTA, induction of vascular endothelial growth factor (VEGF) mRNA expression by saRNA was also examined. A 21-nucleotide saRNA (saVEGF-706) targeting the VEGF promoter at position −706 relative to the transcriptional start site of VEGF was designed and chemically synthesized. The saRNA were transfected into HeLa cells for 72 hours. RNA was extracted using RNeasy kit (Qiagen). Total cellular RNA (1 μg) was reverse transcripted using SuperScript™ reverse transcriptase (Invitrogen) and oligo(dT) primer. The resulted cDNA was amplified using VEGF primers which amplify simultaneously two isoforms (VEGF 189 and 165). Compared to mock transfected cells, saVEGF-706 transfected cells showed a 3.7 and 4-fold increase in VEGF 189 and VEGF 165 mRNA expression respectively; while a control saRNA did not have any effect on VEGF expression (FIG. 12).

Example 8

Analysis of saRNA Complementarity to Target Sequence

To analyze the complementarity of the saRNA molecules to a target site, two mutant saRNA molecules based on the saEcad-P2 molecule were generated. The mutant saRNA molecules either contained five base pair mismatches in the 5' end relative to the antisense strand of dsEcad-P2 (saEcad-P2-5) or five base pair mismatches in the 3' end (saEcad-P2-3). A schematic of the saRNA is provided in FIG. 13, panels A-C. PC-3 cells were transfected with 50 nM of each saRNA, cultured for 72 hours, and expression of E-cadherin and β-actin was determined by Western blot analysis.

Figure 13:
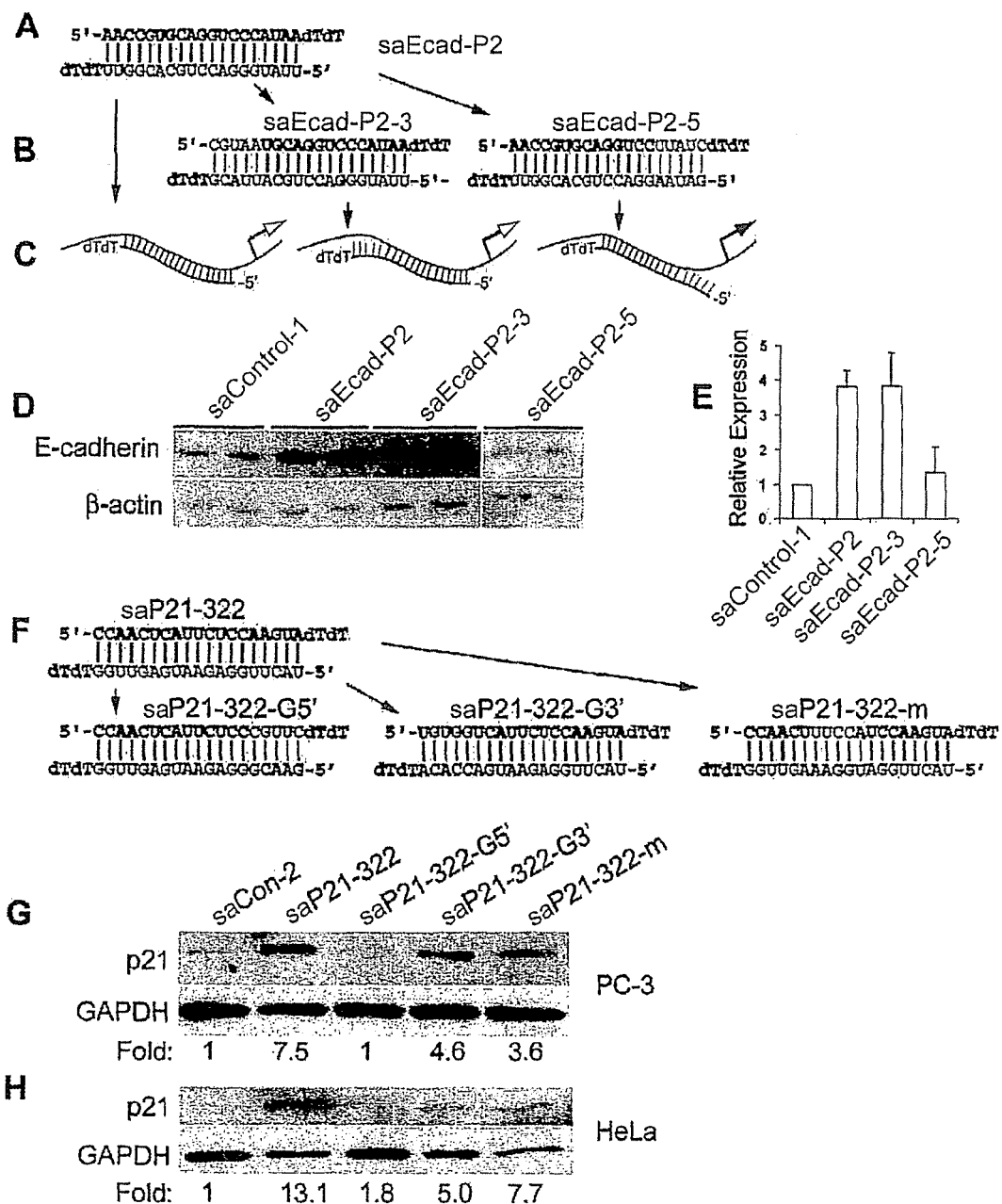
FIG. 13 shows the sequence specificity for saRNA-induced transcriptional activation. Panel A shows the sequence for E-cadherin saRNA saEcad-P2 (sense strand—SEQ ID NO: 5; antisense strand—SEQ ID NO: 6). Panel B shows the sequences of mutated saEcad-P2 molecules. Mutation of the first and last five base pairs of saEcad-P2 duplex resulted in saEcad-P2-3 (sense strand—SEQ ID NO: 9; antisense strand—SEQ ID NO: 10) and saEcad-P2-5 (sense strand—SEQ ID NO: 7; antisense strand—SEQ ID NO: 8), respectively. Panel C schematically exemplifies the mismatch between saEcad-P2-3 and saEcad-P2-5 antisense RNA strand and its target DNA sequence at its 3'- and 5'-ends, respectively. The open bent arrows denote induced transcription, while the closed black bent arrow designates unaffected transcription. Panel D shows the expression level by Western blot of E-cadherin and β-actin in PC-3 cells that were transfected with 50 nM of the indicated saRNA molecules for 72 hours. Panel E is graph showing E-cadherin levels from corresponding Western blots that were normalized to β-actin and presented as the mean±SEM of two independent experiments. Panel F shows the sequence of saP21-322 (sense strand—SEQ ID NO: 23; antisense strand—SEQ ID NO: 24) and its corresponding mutated saRNAs ((saP21-322-G5': sense strand—SEQ ID NO: 25; antisense strand—SEQ ID NO: 26); (saP21-322-G3': sense strand—SEQ ID NO: 27; antisense strand—SEQ ID NO: 28); saP21-322-m: sense strand—SEQ ID NO: 29; antisense strand—SEQ ID NO: 30)). Panel G and Panel H shows the expression level Western blot of p21 and GADPH in either PC-3 cells (Panel G) or HeLa cells (Panel H) that were transfected with 50 nM of the indicated saRNA molecules for 72 hours.

The results show that saEcad-P2 caused significant increase in E-cadherin expression (FIG. 13, panel D and E, lane 3 and 4). Mutations to the 5 base pairs at the 3' end of saEcad-P2 antisense strand (saEcad-P2-3) did not affect saEcad-P2's effect on E-cadherin activation (FIG. 13, panel D and E, lane 5 and 6), while mutation to the 5' end of saEcad-P2 antisense strand (saEcad-P2-5) totally disrupted saEcad-P2's effect (FIG. 13, panel D and E, lane 7 and 8).

Three mutant saRNAs derived from saP21-322 were also tested in PC-3 and HeLa cells, including a 5-bp mutant at the 5'-end (saP21-322-G5', relative to the antisense strand), a 5-bp mutant at the 3'-end (saP21-322-G3'), and a 5-bp mutant in the middle region (saP21-322-m) (FIG. 13, panel F). Consistent with results from the E-cadherin saRNA mutation analysis, mutations to the 5'-end of the saP21-322 antisense strand (saP21-322-05') abolished its ability to activate p21 expression in both PC-3 and HeLa cells (FIG. 13, panels G and H). Mutations to either the 3'-end or middle region retained, to varying extents, the ability to activate p21 (FIG. 13, panels G and H). These results show that the 5'-portion ("seed" sequence) of the antisense strand in saEcad-P2 and dsaP21-322 is critical for initiating transcriptional activation, whereas mismatches to the 3'-end or middle region are tolerated (FIG. 13, panel C).

Accordingly, the results show that saRNA directed transcriptional activation is highly sequence specific and the action of saRNAs is associated with binding of the antisense strand to its target site on the non-coding DNA sequence. In addition, the results show that a saRNA having a region of complementarity as little as 14 nucleotides can induce RdTA.

Example 9 saRNA Size and Gene Activation

Figure 14:
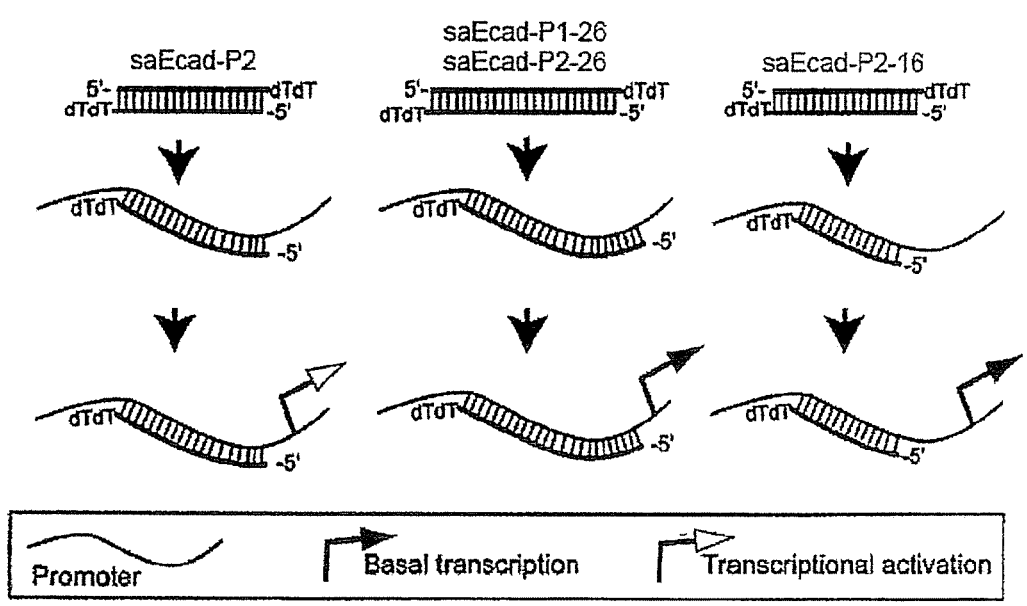
FIG. 14, panel A shows a schematic representation of saRNA size requirement for a particular embodiment. Panel B is a Western blot showing E-cadherin protein expression in PC-3 cells transfected with saRNA of different length. Cells were transfected and cultured with 50 nM saRNA as indicated for 72 hours. saEcad-P2 caused increased expression of E-cadherin, while 26-nt saEcad-P1-26, saEcad-P2-26 and 16-nt saEcad-P2-16 were not as efficient in increasing expression of E-cadherin. Panel C shows E-cadherin protein levels from Panel B normalized to GADPH levels and plotted as fold changes relative to saControl-1 treated cells.
Figure 14:
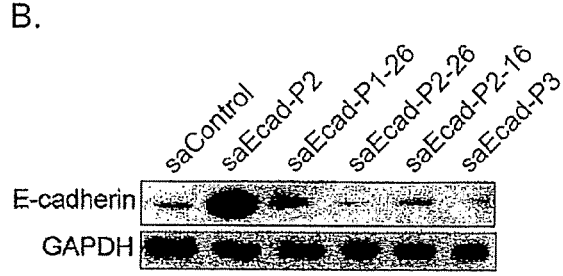
Figure 14:
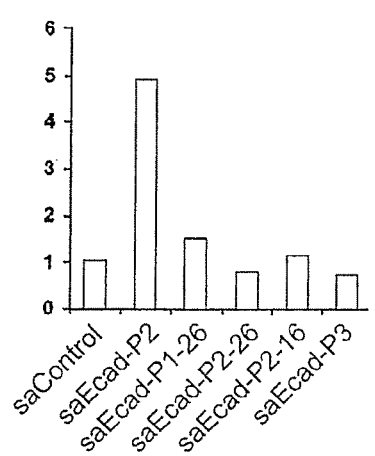

To examine the sequence requirement for RdTA, saRNAs were generated that were either 26 nucleotides in length (saEcad-P1-26 and saEcad-P2-26) or were truncated at 16 nucleotides in length (saEcad-P2-16). FIG. 14, panel A shows a Schematic representation of a 21-nucleotide saRNA targeting the E-cadherin promoter (saEcad-P2), a 26-nucleotide saRNA targeting the E-cadherin promoter (saEcad-P1-26 and saEcad-P2-26), and a 16-nucleotide saRNA targeting the E-cadherin promoter (saEcad-P2-16).

PC-3 cells were transfected with 50 nM of the saRNA as indicated, cultured for 72 hours and expression of E-cadherin was determined by Western blot analysis. The results show that while saEcad-P2 (FIG. 14, panel B, lane 2) caused increased expression of E-cadherin, the 26 nucleotide saEcad-P1-26 (FIG. 14, panel B, lane 3), saEcad-P2-26 (FIG. 14, panel B, lane 4) and 16 nucleotide saEcad-P2-16 (FIG. 14, panel B, lane 5) were not as efficient at activating expression of E-cadherin as the 21-nucleotide saEcad-P2. These results are further exemplified in FIG. 14, panel C, which shows E-cadherin protein levels normalized to GADPH and plotted as fold changes relative to saControl treated cells. These results indicate that saRNA of approximately 21-nucleotides in size are preferable for RdTA.

Example 10 saRNAs Targeting the CpG Island (GC-Rich Area) of the E-Cadherin Promoter Fail to Induce E-Cadherin Transcription To analyze the target requirement for saRNA induced transcriptional activation, three additional saRNA molecules (saEcad-837, saEcad-947 and saEcad-962) were generated targeting the CpG island area of the E-cadherin promoter or having a high GC content. A schematic of the positioning of the saRNA molecules is provided in FIG. 15, panel A. PC-3 cells were transfected with 50 nM of each saRNA, cultured for 72 hours, and expression of E-cadherin was determined by Western blot analysis.

Figure 15:
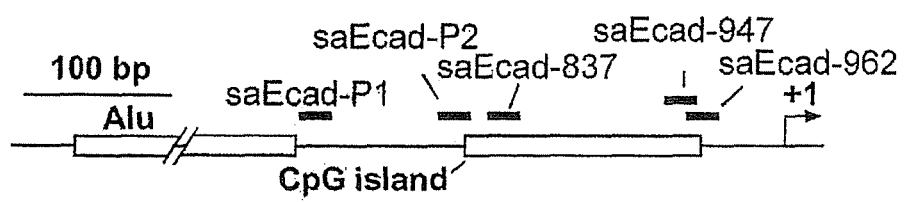
FIG. 15, panel A shows a schematic model of target requirement for saRNA induced transcriptional activation with respect to CpG islands. Panel B shows a Western blot in the top panel showing expression of E-cadherin and GADPH in PC-3 cells transfected and cultured with 50 nM saRNA as indicated for 72 hours. saEcad-P2 induced E-cadherin transcription (lane 2) while saEcad-837, -947 and -962 show no induction (lane 3, 4 and 5). The bottom panel of Panel B shows E-cadherin levels normalized to GADPH and plotted as fold increase relative to mock transfections.
Figure 15:
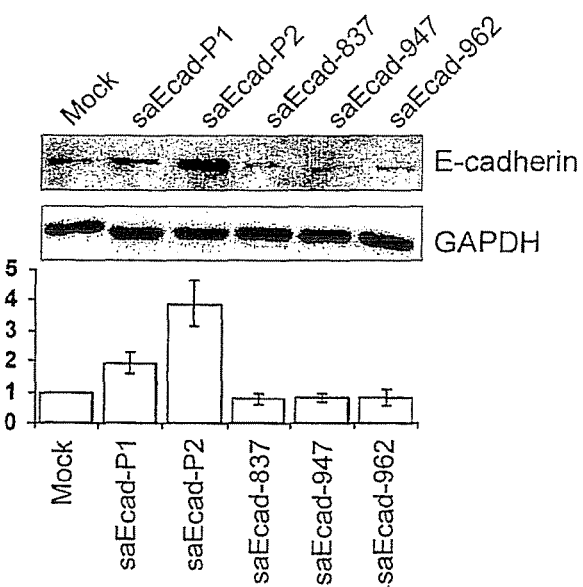

The results show that saEcad-P1 and saEcad-P2 induced E-cadherin transcription (FIG. 15, panel B, lanes 2 and 3) while saEcad-837, -947 and -962, which target the CpG island, show no induction (FIG. 15, panel B, lane 4, 5 and 6). The bottom panel of Panel B of FIG. 15 shows E-cadherin levels normalized to GADPH and plotted as fold increase relative to mock transfections. Therefore, the results show that saRNA targeting the CpG island or a GC-rich region of a nucleic acid sequence do not provide for detectable gene activation.

Example 11 saRNA Induces Expression of Tumor Suppressor Gene p21 and Inhibition of Tumor Growth In Vivo A xenograft prostate cancer model was established by inoculating $5.0 \times 10^6$ PC-3 prostate cancer cells into the lower flank of twelve four-week-old athymic nude, homozygous male mice. saP21-322 (40 mg) in the formula of polyethylenimine-saRNA complex was injected intratumorally into mice with established xenograft tumor (~55 mm³) every 3 days for nine days for a total of 3 injections. The mice were sacrificed on week 4 after initiation of treatment.

Figure 16:
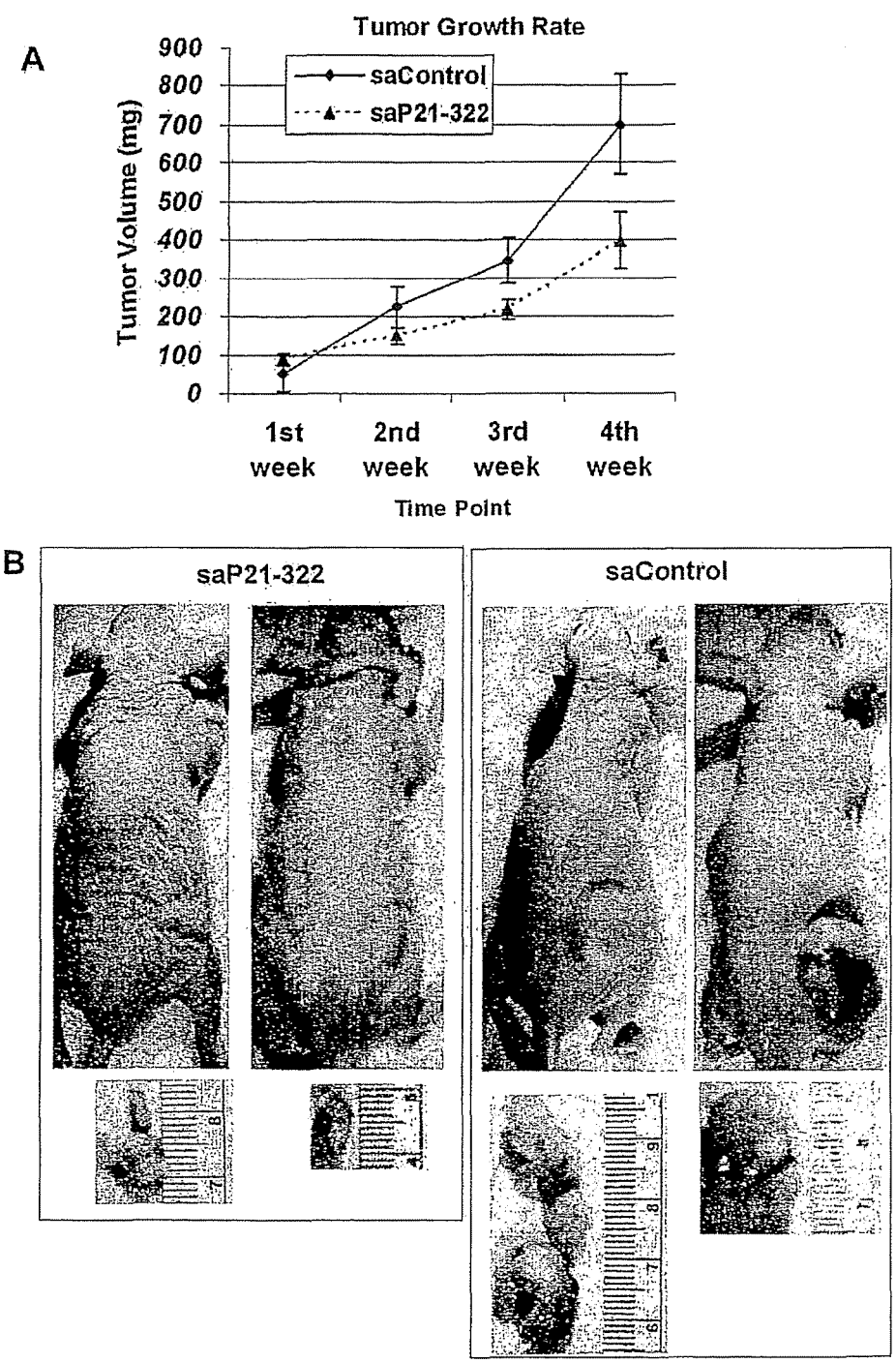
FIG. 16 shows the antitumor effect of saP21-322 saRNA in mouse prostate cancer xenograft tumor models. Mice with established tumors received intratumoral injection of PEI-saRNA complex every 3 days for nine days for a total of 3 injections. Panel A is a graph showing tumor growth curves. Tumor size was measured every week using digital calipers. Results are presented as means±SD (n=6 tumors). Panel B is a picture of mice and tumors at sacrifice at week 4 following the initial saRNA injection. Two representative mice and their tumors are shown in saControl and saP21-322 treatment group.

As shown in FIG. 16, Panel A, at week one following the initial saRNA injection, slower tumor growth was observed in saRNA treated mice compared to saControl group mice (149 vs 224 nag). At week four, the difference in tumor size between saP21-322 and saControl treated groups reached the greatest (397.5 vs 700 mg) (FIG. 16, Panel A and B). There was no significant difference in mice body weight between these two groups. The results show that saRNA directed to the tumor suppressor gene p21 activates gene expression and mediates inhibition of tumor growth as compared to the control.

Figure 17:
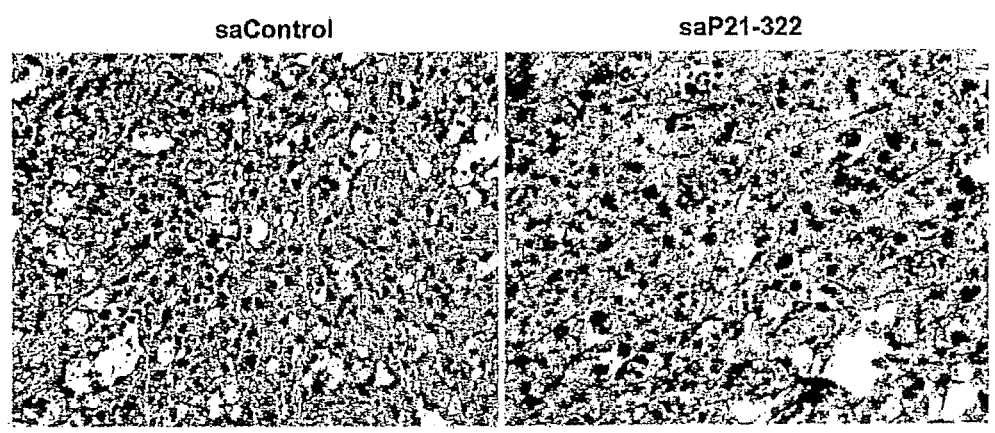
FIG. 17 shows that saP21-322 induces p21 expression in vivo. Mice with established tumors received intratumoral injection of PEI-saRNA complex every 3 days for nine days for a total of 3 injections. Immunostaining was performed on tumor tissue sections using anti-p21 antibody. Cells in saControl group tumors are negative for p21 staining whereas the majority of cells in saP21-322 group tumors show positive nuclear staining of p21.

To verify that the observed antitumor effect of saP21-322 was mediated by activating p21 expression in tumor cells, p21 expression was evaluated in the mice tumors by immunohistochemistry staining using anti-p21 antibody. As shown in FIG. 17, there is no positive staining for p21 in saControl group tumors, while the majority of cells show typical nuclear staining for p21 in saP21-322 treated tumors. The results show that saRNA indeed activates p21 expression in vivo.

Example 12

Transcriptional Induction by saRNA Requires Argonaute2 Protein

In RNAi, there are two known RNAi effector complexes, RISC and RITS (RNA-induced initiation of transcriptional gene silencing). A core component common to both complexes is the Argonaute (Ago) family protein which functions in both target recognition and mRNA cleavage. In human cells, Ago2 is the sole Ago member in RISC (Liu, et al. *Science* 305, 1437-41 (2004).). To test whether RdTA is mediated by the Ago2 protein or by direct interaction between saRNA and its target DNA sequence, we used a siRNA to knock down Ago2 expression and examined if saRNA could still stimulate E-cadherin and p21 transcription in the absence of Ago2. An Ago2 specific siRNAs (siAgo2) and a control siRNA (siAgo-C) were used. The control siRNA molecules siAgo-C is similar to siAgo2 in terms of composition and terminal modification but contains random sequence.

Figure 18:
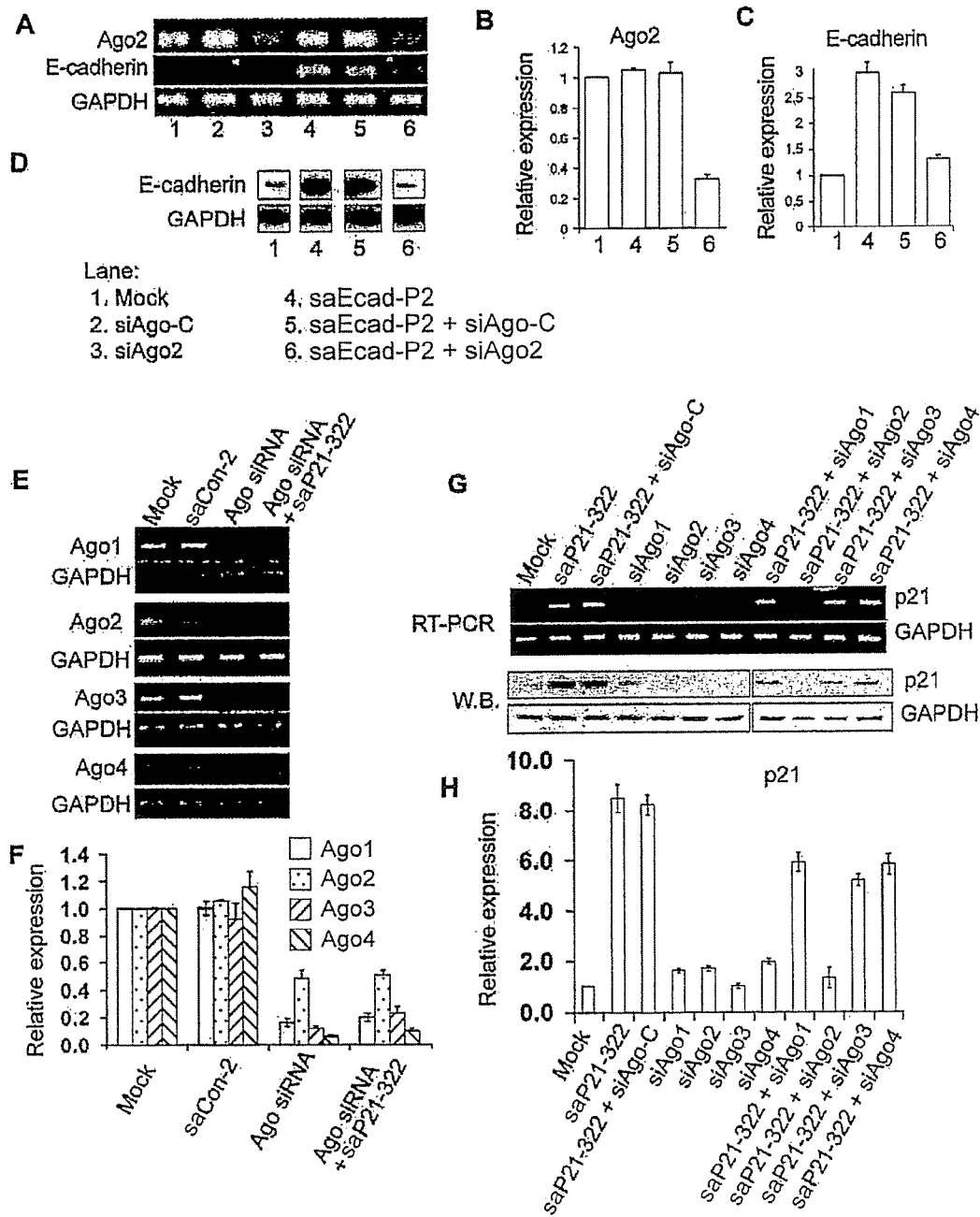
FIG. 18 shows saRNA-induced transcriptional activation requires the Ago2 protein. Panel A shows results of PC-3 cells transfected with 50 nM of each saRNA as indicated for 60 hours. The mRNA expression of E-cadherin, Ago2, and GAPDH were determined by RT-PCR. Panel B and Panel C show E-cadherin and Ago2 mRNA expression normalized to GAPDH levels. The results are presented as the mean±SEM of two independent experiments. Panel D shows the protein levels of E-cadherin and GAPDH detected by Western blot analysis in PC-3 cells as treated in Panel A. Panel E shows results of PC-3 cells that were transfected with 50 nM of the indicated saRNA and/or siRNA molecules for 72 hours. The mRNA expression of Ago1-4 was assessed by RT-PCR. Each Ago family member was knocked down by their corresponding Ago siRNA (siAgo1, 2, 3, or 4). Panel F is a graph showing the RT-PCR results normalized to GAPDH expression levels and presented as the mean±SEM from two independent experiments. Panel G shows results of PC-3 cells transfected with 50 nM of each indicated saRNA for 72 hrs. Both p21 and GAPDH mRNA and protein levels were determined by RT-PCR and Western blot (W.B.) analysis, respectively. Panel H is graph showing p21 mRNA levels normalized to GAPDH and presented as the mean±SEM from at least two independent experiments (containing two sample repeats per experiment).

PC-3 cells were transfected and cultured for 60 hours using the following siRNAs or saRNA alone or in combination: siAgo2, siAgo-C, saEcad-P2. As shown in FIG. 18, Panel A, siAgo2 significantly knocked down Ago2 expression alone by approximately 70% (lane 3), while a control siRNA (siAgo-C) did not (lane 2). E-cadherin saRNA alone or in combination with siAgo-C induced significant expression of E-cadherin transcription (FIG. 18, Panel A, lane 4 and 5). However, in Ago2 knocked down cells, saEcad-P2 failed to induce E-cadherin expression (FIG. 18, Panel A, lane 6). FIG. 18, Panel B and Panel C show E-cadherin and Ago2 mRNA expression normalized to GAPDH levels. The results are presented as the mean±SEM of two independent experiments. In addition, FIG. 18 Panel D shows the protein levels of E-cadherin and GAPDH detected by Western blot analysis in PC-3 cells as treated in Panel A. Therefore, the results show that RdTA depends on Ago2 protein.

In order to evaluate the impact other Ago family members have on RdTA, we targeted Ago1-4 with specific siRNAs (siAgo1, siAgo2, siAgo3, and siAgo4) (Matranga et al., *Cell* 123, 607 (2005). PC-3 cells were transfected using each of the Ago siRNAs alone or in combination with the p21-specific saRNA saP21-322 (FIG. 18, Panels E to H). When each Ago siRNA was co-transfected with saP21-322, only siAgo2 completely prevented p21 induction (FIG. 18, Panels G and H). Knockdown of Ago1, 3, and 4 caused an approximate 0.3-, 0.4-, and 0.3-fold reduction in saRNA-induced p21 expression, respectively (FIG. 18, Panel H). While other Ago family members may play supportive roles in RdTA, Ago2 is indispensable for saRNA-induced gene activation. Consistent with the findings for E-cadherin activation by saRNAs, activation of p21 also requires the Ago2 protein for functioning.

Example 13 saRNAs Induce Loss of Histone Methylation at Lysine 9

Figure 19:
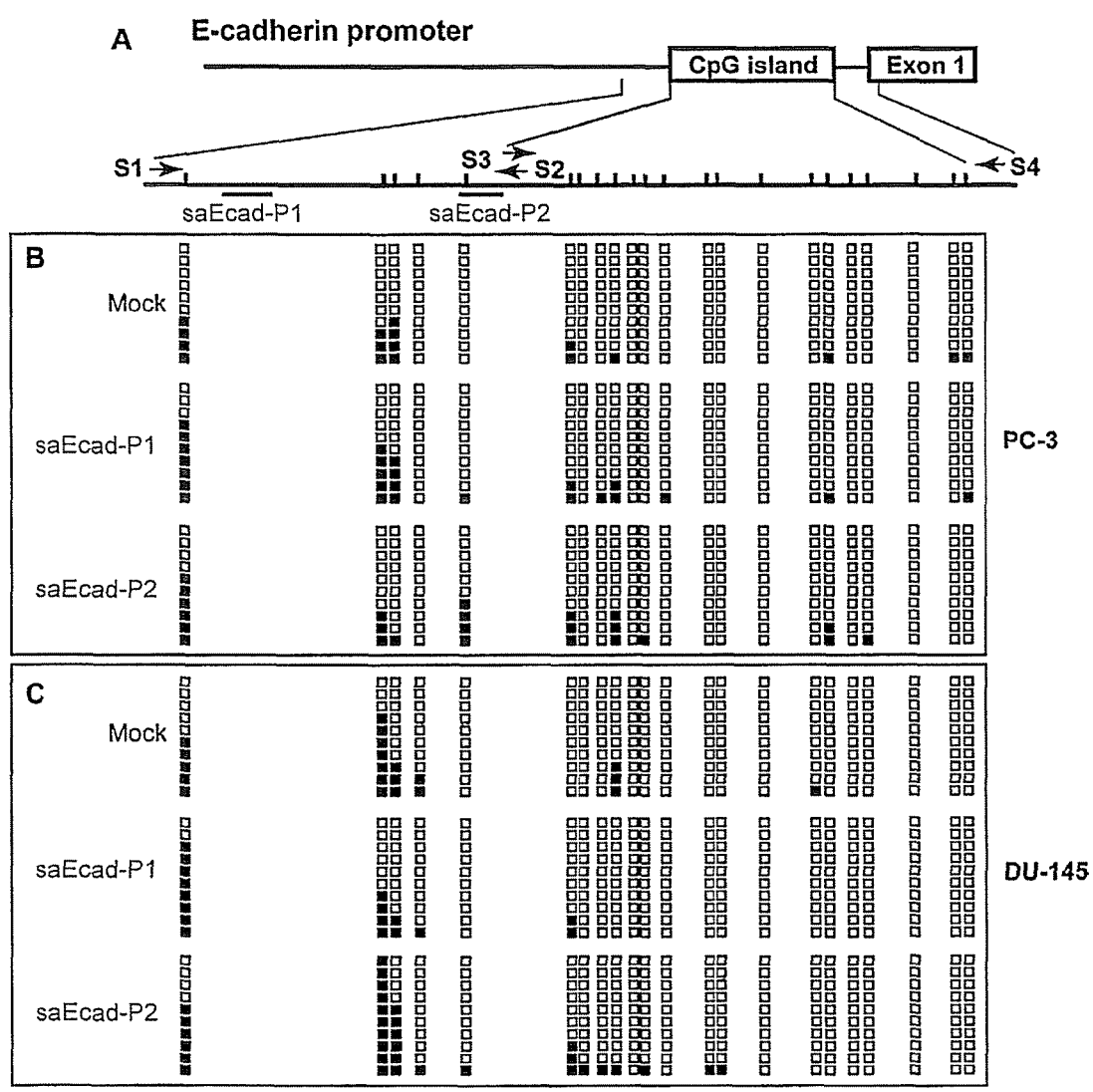
FIG. 19 shows DNA methylation changes of E-cadherin promoter in saRNA transfected PC-3 and DU145 cells. Panel A is a schematic representation of E-cadherin promoter with the CpG sites (vertical bar), saRNA target (short line) and bisulfite genomic sequencing PCR primers (arrow) indicated. Panel B shows the methylation profile of the E-cadherin promoter in mock transfected, saEcad-P1 transfected and saEcad-P2 transfected PC-3 cells respectively. Panel C shows the methylation profile of E-cadherin promoter in mock transfected, saEcad-P1 transfected and saEcad-P2 transfected DU145 cells. Solid circles indicate methylated CpG sites and open circle unmethylated CpG sites.

To examine whether epigenetic changes are mechanism responsible for RdTA, DNA methylation changes in the saRNA-targeted region within the E-cadherin promoter was first assessed using bisulfite genomic sequencing. The CpG island within the E-cadherin promoter is essentially unmethylated in mock transfected PC-3 and DU145 cells (FIG. 19, panel B). In saRNA transfected PC-3 and DU145 cells, a slight increase in CpG methylation was observed which was confined to the CpG sites adjacent to (saEcad-P1) (FIG. 19, panel B and C) or within the target sequence (saEcad-P2) (FIG. 19, panel B and C), showing that saRNA induced methylation does not spread across the DNA. This finding is consistent with observations in RNA directed DNA methylation (RdDM) in plants (Pelissier et al., *Nucleic Acids Res* 27:1625-34 (1999)). The saRNA induced increase in DNA methylation, although not significant, appears to be contradictory to the observed expression induction since hypermethylation of DNA has been associated with transcriptional silencing. A simple explanation for this contradiction is that the two saRNA target sites are outside the E-cadherin CpG island and methylation outside the CpG island has no impact on gene transcription. The ineffectiveness in inducing E-cadherin expression by saEcad-P3 (FIG. 1, panels A and B, and FIG. 2), which targets the CpG island and thus has a higher GC content (84%), provides further support. Therefore, the results show that DNA methylation is unlikely to play a role in saRNA-dependent induction of E-cadherin expression. In addition, non-CpG methylation associated with siRNA treatment was not observed, contrary to a previous report in human cells (Kawasaki et al., *Nature* 431:211-7 (2004)).

Figure 20:
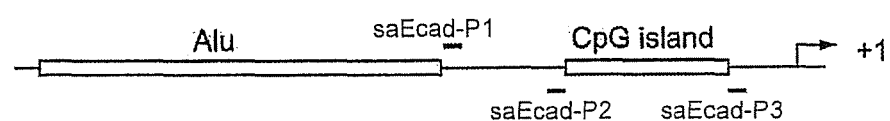
FIG. 20 shows that saRNA-induced transcriptional activation is associated with loss of histone 3 methylation at lysine 9. Panel A shows a schematic representation of the E-cadherin promoter and the location of ChIP PCR. Panel B PC-3 cells were transfected with 50 nM of the indicated saRNA molecules for 72 hrs. ChIP assays were performed using antibodies against H3 m2K9 and H3 m2K4 to pull down associated DNA. The precipitated DNA was amplified by PCR. Input DNA was amplified as a control. No antibody controls are indicated by Ab (−). Panel C is a graph showing the signals of H3 m2K4 and H3 m2K9 normalized to DNA levels in input lanes. The results are the means±SEM of at least two independent experiments.
Figure 20:
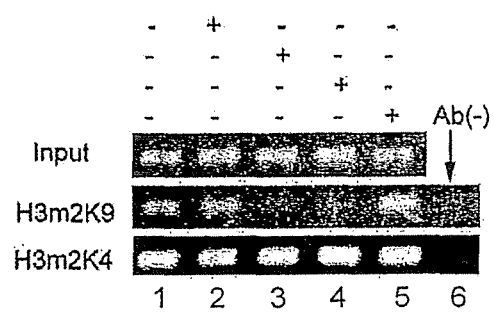
Figure 20:
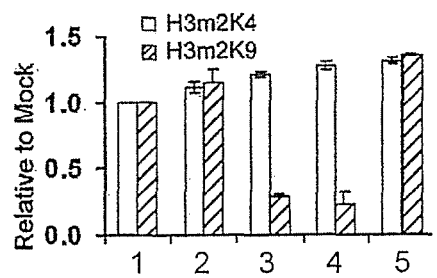

Whether RdTA could be associated with histone-based regulatory mechanisms was next tested. Chromatin immunoprecipitation (ChIP) assays were performed using an antibody that recognizes di-methylated histone 3 at lysine 4 (H3 m7K4) and dimethylation at lysine 9 (H3 m2K9). In mock and saControl transfected cells, a significant amount of genomic DNA corresponding to the E-cadherin promoter was associated with both H3 m2K4 and H3 m2K9 (FIG. 20, Panels A and B). Significantly, in cells transfected with saEcad-P1 or saEcad-P2, the level of methylated histones associated with E-cadherin promoter DNA was decreased by 74% and 80% respectively compared to that in mock transfected cells (FIG. 20, Panels B and C). The magnitude of H3 m2K9 loss corresponded inversely to E-cadherin expression induction. However, a similar change was not observed in H3 m2K4 in any of the saRNA treated cells (FIG. 20, Panels B and C). The results show that treatment of cells with saEcad-P1 or saEcad-P2 results in demethylation of H3 m2K9 on the E-cadherin promoter.

Such demethylation may lead to chromatin remodelling and transcriptional induction (Nguyen et al., Cancer Res 62, 6456-61 (2002)). Based on the results, it is observed that once saRNA is introduced into the nucleus, an effector complex (Verdel et al., *Science* 303:672-6 (2004)) involving the Ago2 protein, is formed which further recruit other enzymes that may demethylate histone thereby affecting RdTA. In this regard, an enzyme that regulates histone arginine and lysine demethylation has recently been identified (Wang et al., *Science* 306:279-83 (2004); Shi et al., *Cell* 119:941-953 (2004)). Other possibilities could not be ruled out, such as targeted degradation of methylated histones, replacement of methylated histones by unmethylated variants and clipping of histone tails by proteases (Bannister et al., *Cell* 109:801-6 (2002); Orphanides et al., *Cell* 108:439-51 (2002); Zhang et al., *Nature* 431:637-9(2004)).

Example 14 saRNAs do not Cause Interferon Response

Figure 21:
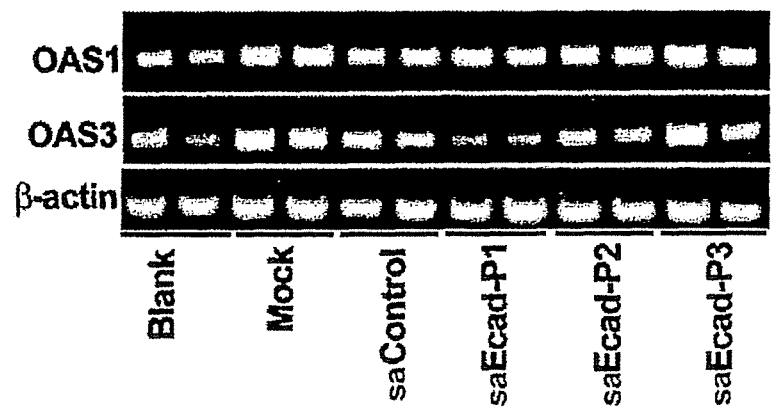
FIG. 21, Panel A shows that saRNAs do not induce interferon response genes. Cells were transfected for 72 hours using Lipofectamine 2000 (Invitrogen) as the transfection reagent. OAS1 and OAS3 mRNA expression was analyzed by RT-PCR. The β-actin gene was also amplified as a control for RNA loading. Panel B is a graph showing the relative expression for the indicated samples of panel A. The results were means±SEM of two independent experiments with duplicate samples in each experiment (Blank: medium only; Mock: Lipofectamine only). Panel C shows the mRNA expression level of OAS1, OAS2, p21, E-cadherin, and GADPH analyzed by RT-PCR in PC-3 cells that were treated with interferon-α2a (IFN-α2a) at the specified concentrations for 24 hours.
Figure 21:
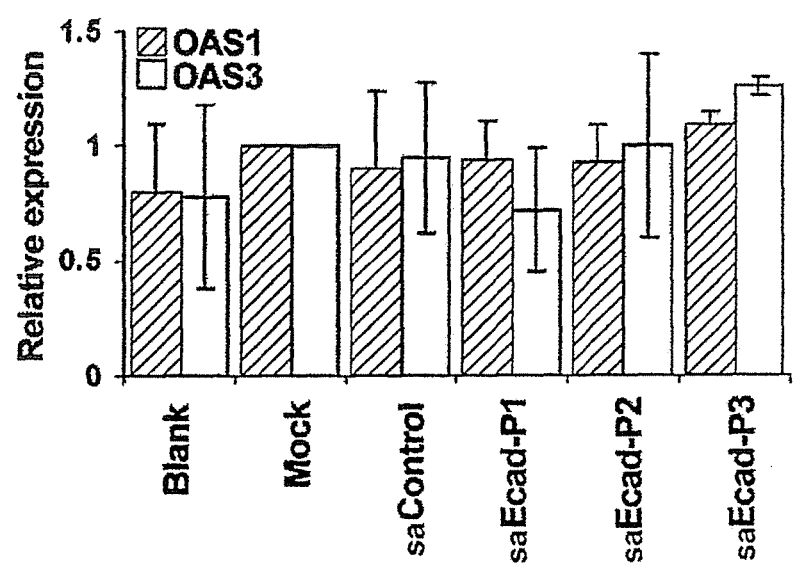
Figure 21:
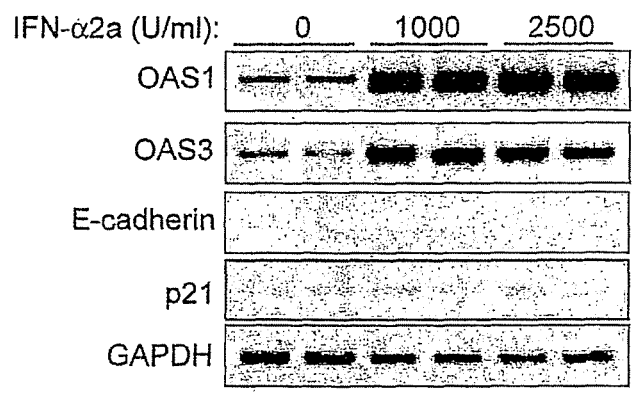

To rule out the possibility that an interferon response may be responsible for the observed induction of E-cadherin expression by saRNAs, the expression of two classic interferon response genes, OAS1 and OAS3, was analyzed which can be induced by some siRNAs (Bridge et al., Nat Genet. 34:263-4 (2003); Sledz et al., Nat Cell Biol 5:834-9 (2003)). The results show that the level of OAS1 and OAS3 mRNA expression was not influenced by any of the saRNAs (FIG. 21, Panels A and B). Similarly, the expression of two housekeeping genes β-actin and GAPDH was also unaffected in any of the saRNA transfection experiments. In addition, PC-3 cells were treated with type I interferon-α2a (IFN-α2a) to determine if E-cadherin and p21 expression is susceptible to interferon treatment. As shown in FIG. 21, Panel C, there was no observable change in the expression of E-cadherin and p21 in the treated cells whereas OSA1 and OAS3 are readily induced by interferon treatment.

Therefore, the results show that an interferon response is not involved in the induction of E-cadherin and p21 by saRNA. Instead, the results provide an explanation for some of the off-target effects observed in RNAi experiments (Scacheri et al., Proc Natl. Acad. Sci. USA 101:1892-7 (2004)), in which homology between siRNAs and non-coding sequences may occur. Thus some siRNAs may generate unintended effects by initiating transcriptional activation or silencing of genes whose promoter sequence resembles that of the siRNA.

Example 15 saRNAs do not Target Cryptic Promoter Transcription

Figure 22:
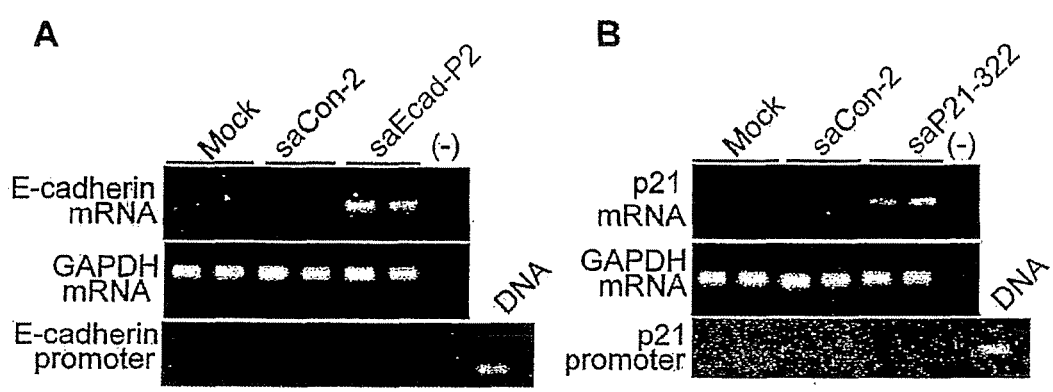
FIG. 22 shows an analysis of the p21 and E-cadherin promoters for cryptic transcripts. Panel A shows PCR based detection of E-cadherin and GADPH expression in PC-3 cells. Total cellular RNA was isolated from PC-3 cells transfected with Mock, saCon-2, or saEcad-P2 for 72 hrs. One microgram of total RNA was treated with DNase I and reverse transcribed using random hexamer primers. Expression of E-cadherin and GAPDH was detected using gene specific primer sets. No cryptic transcript was detected using primers complementary to the E-cadherin promoter. Genomic DNA (DNA) served as a positive control. Panel B shows PCR based detection of p21 and GADPH expression in PC-3 cells. PC-3 cells were transfected with Mock, saCon-2, or saP21-322 as indicated for 72 hours. Expression levels of p21 and GAPDH were determined by RT-PCR as described in Panel A. No cryptic transcript was amplified in the p21 promoter.

To determine if cryptic transcripts derived from promoter regions may have been the actual targets of saRNAs, an RT-PCR analysis was performed using primers specific to p21 and E-cadherin promoter sequences. Total cellular RNA was isolated from PC-3 cells transfected with mock, saCon-2, saEcad-P2, or saP21-322 for 72 hours. One microgram of total RNA was treated with DNase I and reverse transcribed using random hexamer primers. Expression of E-cadherin, p21 and GAPDH was detected using gene specific primer sets. No cryptic transcript was detected using primers complementary to the E-cadherin promoter as shown in FIG. 22, panel A. In addition, no cryptic transcript was amplified in the p21 promoter as shown in FIG. 22, panel B. Therefore, the results show that saRNA-induced transcription is activated through targeting the promoter.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An isolated composition comprising a double stranded small activating RNA (saRNA) molecule of 19 base pairs in length, wherein the saRNA molecule comprises a first ribonucleic acid strand comprising the sequence of SEQ ID NO:32, wherein the saRNA molecule increases expression of the VEGF gene when introduced into a cell.

2. The composition of claim 1, wherein the saRNA molecule is encoded on a nucleic acid vector.

3. The composition of claim 1, wherein the saRNA molecule comprises a thio modified internucleotide linkage.

4. An isolated composition comprising:
   a double stranded small activating RNA (saRNA) molecule 19 base pairs in length, wherein the saRNA molecule comprises a first ribonucleic acid strand comprising the sequence of SEQ ID NO:32 and a second ribonucleic acid strand comprising the sequence of SEQ ID NO:31; and at least one of a pharmaceutically acceptable carrier, a pharmaceutically acceptable diluent, a pharmaceutically acceptable excipient and a pharmaceutically acceptable adjuvant,
   wherein the saRNA molecule increases expression of the VEGF gene when introduced into a cell.

5. A method to increase expression of vascular endothelial growth factor (VEGF) gene in a mammalian cell, the method comprising:
   introducing the composition of claim 1 into the mammalian cell in an amount sufficient to increase expression of the VEGF gene.

6. The method of claim 5, wherein the composition is introduced into the mammalian cell by expression from the nucleic acid vector of claim 2 transfected into the mammalian cell.

7. The method of claim 5, wherein the composition comprises the saRNA molecule of claim 2.

* * * * *